United States Patent
Munoz et al.

(10) Patent No.: US 8,420,622 B2
(45) Date of Patent: *Apr. 16, 2013

(54) SILYLATED PIPERIDINE DERIVATIVES

(75) Inventors: Benito Munoz, Newtonville, MA (US); Jed Hubbs, Cambridge, MA (US); Christopher L. Hamblett, Boston, MA (US); Hua Zhou, Waltham, MA (US); Michelle Martinez, Salem, MA (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 625 days.

This patent is subject to a terminal disclaimer.

(21) Appl. No.: 12/520,132

(22) PCT Filed: Dec. 14, 2007

(86) PCT No.: PCT/US2007/025639
§ 371 (c)(1),
(2), (4) Date: Oct. 22, 2009

(87) PCT Pub. No.: WO2008/085301
PCT Pub. Date: Jul. 17, 2008

(65) Prior Publication Data
US 2010/0093665 A1   Apr. 15, 2010

Related U.S. Application Data

(60) Provisional application No. 60/876,023, filed on Dec. 20, 2006.

(51) Int. Cl.
*A61K 31/445* (2006.01)
*C07F 7/10* (2006.01)

(52) U.S. Cl.
USPC ............... 514/63; 514/317; 514/326; 546/14; 546/210; 546/237

(58) Field of Classification Search ........... 514/317, 514/326, 63; 546/210, 237, 14
See application file for complete search history.

(56) References Cited

U.S. PATENT DOCUMENTS

| 5,760,018 | A | 6/1998 | Baker et al. | |
|---|---|---|---|---|
| 7,638,629 | B2 * | 12/2009 | Hannam et al. | 546/124 |
| 2009/0239905 | A1 * | 9/2009 | Hannam et al. | 514/314 |
| 2010/0093665 | A1 * | 4/2010 | Munoz et al. | 514/63 |

FOREIGN PATENT DOCUMENTS

| WO | 2006043064 A1 | 4/2006 |
|---|---|---|
| WO | WO 2006/043064 A1 | 4/2006 |
| WO | 2007110667 A1 | 10/2007 |
| WO | 2007116228 A1 | 10/2007 |
| WO | 2007125364 A1 | 11/2007 |
| WO | 2008030391 A2 | 3/2008 |

OTHER PUBLICATIONS

Braga et al. "Making crystals from . . . " J. Roy. Soc. Chem. Chem. Commun. p. 3635-3645 (2005).*
Esler et al. "Transition state . . . " Nature Cell Biol. v. 2, p. 428-434 (2000).*
Garofalo "Patents targeting . . . " Exp. Opinion Ther. Patents 18(7) 693-703 (2008).*
Heike et al. "Design synthesis . . . " J. Med. Chem. v. 53, p. 4691-4700 (2010).*
Szekely et al. "Prevention of Alzheimer . . . " Int. Rev. Psych. v. 19(6) p. 693-706 (2007).*
European Search Report dated Mar. 14, 2010, mailed on Mar. 24, 2011 for related International Application No. EP 07 85 3393; 4 pages.
Copending U.S. Appl. No. 12/294,303, filed Mar. 27, 2007, U.S. National Stage Entry of PCT/GB07/050155, published as WO07/110667.
Copending U.S. Appl. No. 12/298,394, filed Apr. 25, 2007, U.S. National Stage Entry of PCT/GB07/050213, published as WO07/125364.
Copending U.S. Appl. No. 12/296,365, filed Apr. 2, 2007, U. S. National Stage Entry of PCT/GB07/050176, published as WO07/116228.
Copending U.S. Appl. No. 12/439,010, filed Aug. 31, 2007, U.S. National Stage Entry of PCT/GB08/030391 published as WO08/030391.

* cited by examiner

*Primary Examiner* — Celia Chang
(74) *Attorney, Agent, or Firm* — Susan L. Hess; Gerard M. Devlin; Raynard Yuro

(57) ABSTRACT

Compounds of formula I: I wherein at least one of R4 and R5 comprises Si(R6)3 as a substituent selectively attenuate production of Aβ(1-42) and hence find use in treatment of Alzheimer's disease and related conditions.

9 Claims, No Drawings

SILYLATED PIPERIDINE DERIVATIVES

CROSS REFERENCE TO RELATED APPLICATIONS

This application is a U.S. National Phase application under 35 U.S.C. §371 of PCT Application No. PCT/US2007/025639, filed Dec. 14, 2007, which claims priority under 35 U.S.C. §119(e) from U.S. Provisional Application No. 60/876,023, filed Dec. 20, 2006.

This invention relates to compounds for use in therapeutic treatment of the human body. In particular, it provides carboxy-functional 1,2-disubstituted piperidines and related compounds useful for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, *PNAS,* 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral haemorrhage with amyloidosis, Dutch-type (HCHWA-D), multi-infarct dementia, dementia pugilistica and Down syndrome.

Various interventions in the plaque-forming process have been proposed as therapeutic treatments for AD (see, for example, Hardy and Selkoe, *Science,* 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Phiel et al, *Nature,* 423 (2003), 435-9). Other proposed methods of treatment include administering a compound which blocks the aggregation of Aβ, and administering an antibody which selectively binds to Aβ.

However, recent reports (Pearson and Peers, *J. Physiol.,* 575.1 (2006), 5-10) suggest that Aβ may exert important physiological effects independent of its role in AD, implying that blocking its production may lead to undesirable side effects. Furthermore, γ-secretase is known to act on several different substrates apart from APP (e.g. notch), and so inhibition thereof may also lead to unwanted side effects. There is therefore an interest in methods of treating AD that do not suppress completely the production of Aβ, and do not inhibit the action of γ-secretase.

One such proposed treatment involves modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and US 2002/0128319 and Weggen et al *Nature,* 414 (2001) 212-16; Morihara et al, *J. Neurochem.,* 83 (2002), 1009-12; and Takahashi et al, *J. Biol. Chem.,* 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce intracerebral Aβ deposition in animal models (WO 02/092072; Jantzen et al, *J. Neuroscience,* 22 (2002), 226-54). US 2002/0015941 teaches that agents which potentiate capacitative calcium entry activity can lower Aβ(1-42).

Further classes of compounds capable of selectively attenuating Aβ(1-42) production are disclosed on WO 2005/054193, WO 2005/013985, WO 2006/008558, WO 2005/108362 and WO 2006/043064. The aforementioned WO 2006/043064 discloses inter alia various N-substituted piperidinylacetic acid derivatives, but neither discloses nor suggests the compounds of the present invention.

The compounds of the present invention selectively attenuate Aβ(1-42) production with high potency and a reduced propensity for undesirable side effects.

According to the present invention there is provided a compound of formula I:

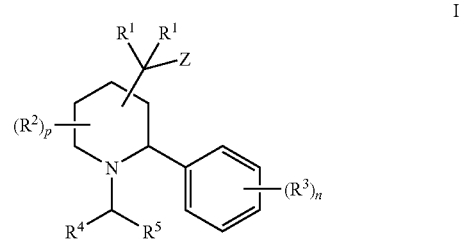

or a pharmaceutically acceptable salt or hydrate thereof; wherein:

p is 0, 1 or 2;
n is 0, 1, 2 or 3;
the moiety —C(R$^1$)$_2$—Z is attached to the 3-, 4- or 5-position of the piperidine ring;
Z represents CO$_2$H or a tetrazole ring;
each R$^1$ independently represents H or a non-aromatic hydrocarbon group of up to 6 carbon atoms; or the two R$^1$ groups complete a C$_{3-6}$alicyclic group;
each R$^2$ independently represents a non-aromatic hydrocarbon group of up to 6 carbon atoms; or two R$^2$ groups attached to adjacent ring carbon atoms may complete a fused carbocyclic ring of up to 7 atoms;
each R$^3$ independently represents halogen, C$_{1-6}$alkyl bearing 0-3 fluorine substituents, C$_{1-6}$alkoxy bearing 0-3 fluorine substituents, C$_{2-6}$alkenyl, or Si(R$^6$)$_3$;
R$^4$ is selected from:
(i) H;

(ii) Het-A- where A represents a bond, $CH_2$ or 1,4-phenylene and Het represents a heterocyclic ring system of up to 10 ring atoms which optionally bears up to 3 substituents selected from halogen, $C_{1-4}$alkyl, $CF_3$, $Si(R^6)_3$, $C_{1-4}$alkoxy and $C_{1-4}$alkoxycarbonyl or which optionally bears a phenyl substituent which itself is optionally substituted with halogen, $C_{1-4}$alkyl, $Si(R^6)_3$, $C_{1-4}$alkoxy or $C_{1-4}$alkoxycarbonyl; and (iii) hydrocarbon of up to 12 carbon atoms which optionally bears up to 3 substituents selected from halogen, perfluoro$C_{1-4}$alkyl, CN, $Si(R^6)_3$, OH, $C_{1-4}$alkoxy and $OCF_3$;

$R^5$ is selected from:

(i) H;

(ii) hydrocarbon of up to 12 carbon atoms which optionally bears up to 3 substituents selected from halogen, perfluoro$C_{1-4}$alkyl, CN, $Si(R^6)_3$, OH, $C_{1-4}$alkoxy and $OCF_3$; and (iii) $CO_2R^7$ where $R^7$ represents hydrocarbon of up to 12 carbon atoms which optionally bears up to 3 substituents selected from halogen, perfluoro$C_{1-4}$alkyl, CN, $Si(R^6)_3$, OH, $C_{1-4}$alkoxy and $OCF_3$; and each $R^6$ independently represents a hydrocarbon group of up to 6 carbon atoms;

provided $R^4$ and $R^5$ do not both represent H and provided at least one of $R^4$ and $R^5$ comprises $Si(R^6)_3$ as a substituent.

In a particular embodiment, each $R^3$ independently represents halogen, $C_{1-6}$alkyl bearing 0-3 fluorine substituents, $C_{1-6}$alkoxy bearing 0-3 fluorine substituents, or $C_{2-6}$alkenyl.

Where a variable occurs more than once in formula I, the identity taken by said variable at any particular occurrence is independent of the identity taken at any other occurrence.

As used herein, the expression "hydrocarbon group" refers to groups consisting solely of carbon and hydrogen atoms. Unless indicated otherwise, such groups may comprise linear, branched or cyclic structures, singly or in any combination consistent with the indicated maximum number of carbon atoms, and may be saturated or unsaturated, including aromatic unless indicated otherwise. Particular examples of hydrocarbon groups include alkyl, alkenyl, alkynyl, cycloalkyl, cycloalkenyl, cycloalkylalkyl and (where permitted) phenyl, alkylphenyl and phenylalkyl.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner.

The expression "perfluoro$C_{1-4}$alkyl" refers to linear or branched alkyl groups of up to 4 carbon atoms in which all the hydrogen atoms are replaced by fluorine atoms.

The expression "$C_{3-6}$alicyclic" refers to cyclic non-aromatic hydrocarbon groups containing from 3 to 6 ring carbon atoms. Examples include cyclopropyl, cyclobutyl, cyclopentenyl, cyclopentyl and cyclohexyl.

The term "heterocyclic" refers to mono- or bicyclic ring systems in which at least one ring atom is selected from N, O and S. Unless indicated otherwise, the term includes both saturated and unsaturated systems, including aromatic systems. Heterocyclic groups may be bonded via a ring carbon or a ring nitrogen, unless otherwise indicated.

The term "halogen" as used herein includes fluorine, chlorine, bromine and iodine, of which fluorine and chlorine are preferred unless otherwise indicated.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, a pharmaceutically acceptable salt may be formed by neutralisation of a carboxylic acid group with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be understood that all the stereoisomeric forms encompassed by formula I, both optical and geometrical, fall within the scope of the invention, singly or as mixtures in any proportion. Thus the moieties:

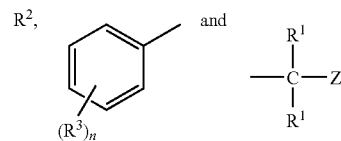

may be in cis- or trans-configurations with respect to the piperidine ring. Furthermore, a given compound in a given cis- or trans-configuration will have two enantiomeric forms, both of which are within the scope of the invention, whether as single homochiral compounds or as racemic mixtures in any proportion. For the avoidance of any doubt, structural formulae such as (A):

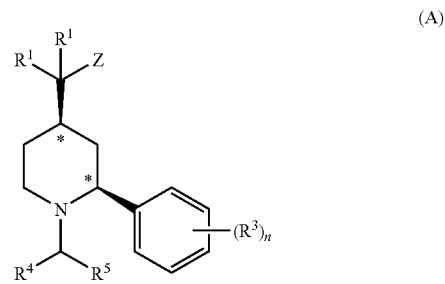

as used herein shall be taken to be definitive of the relative configurations of the carbon atoms marked with asterisks, but not their absolute configurations, unless expressly stated otherwise.

In formula I, the moiety —$C(R^1)_2$—Z is attached to the 3-, 4- or 5-position of the piperidine ring. In a particular embodiment the moiety —$C(R^1)_2$—Z is attached to the 4-position of the piperidine ring.

Z represents $CO_2H$ or a tetrazole ring, in particular, Z represents $CO_2H$ or 1,2,3,4-tetrazol-5-yl, but preferably represents $CO_2H$.

Each $R^1$ independently represents H or a non-aromatic hydrocarbon group of up to 6 carbon atoms; or the two $R^1$ groups complete a $C_{3-6}$alicyclic group (such as cyclopropyl, cyclobutyl, cyclopentenyl or cyclopentyl). In one embodiment, one $R^1$ group is H and the other is H or $C_{1-6}$alkyl such as methyl, ethyl, propyl or butyl. In another embodiment, both $R^1$ groups represent methyl or together complete an alicyclic group. In a further embodiment, both $R^1$ groups represent H.

Groups represented by $R^2$ (when present) may be attached at any available position on the piperidine ring, including the carbon atom to which the moiety —$C(R^1)_2$—Z is attached, but preferably not to the carbon atom to which the moiety $(R^3)_n$—$C_6H_{5-n}$— is attached. In a particular embodiment, p is 0 or 1, and in a further embodiment p is 0 and $R^2$ is absent. Suitable identities for $R^2$ include $C_{1-6}$alkyl such as methyl, ethyl or n-propyl and $C_{2-6}$alkenyl such as allyl.

In an alternative embodiment, p is 2, the $R^2$ groups are attached at adjacent ring positions, and together complete a fused carbocycle of up to 7 atoms. Said fused carbocycle may be fully saturated or may be unsaturated to any degree, including aromatic. Examples include benzene, cyclohexane, cyclopentane and cyclohexane, in particular benzene and cyclohexane.

In formula I, n is preferably 1 or 2, most preferably 1. Each $R^3$ independently represents halogen (especially F), $C_{1-6}$alkyl bearing 0-3 fluorine substituents, $C_{1-6}$alkoxy bearing 0-3 fluorine substituents, $Si(R^6)_3$ (e.g. $SiMe_3$), or $C_{2-6}$alkenyl. When one $R^3$ is present, it is very suitably (but not necessarily) attached in the 4-position. Typical identities for $(R^3)_n$ include 2-$CF_3$, 3-$CF_3$, 4-$CF_3$, 2,4-di($CF_3$), 2-F-4-$CF_3$, 4-$OCF_3$, 4-allyl, 4-$SiMe_3$, 4-n-propyl, 4-isopropyl and 4-tert-butyl. In one embodiment, $(R^3)_n$ represents 4-$CF_3$ or 4-n-propyl, in particular 4-$CF_3$.

In the embodiment wherein $R^4$ represents Het-A, Het typically represents a 5- or 6-membered heterocycle which optionally is fused to a second 5- or 6-membered ring. Said second 5- or 6-membered ring may be carbocyclic or heterocyclic, and when Het represents a group comprising a heterocyclic ring fused to a carbocyclic ring, attachment to the remainder of the molecule may be via either of these rings. Any ring comprised by the group represented by Het may be saturated or unsaturated, including aromatic. Examples of heterocyclic systems within the definition of Het include pyridine, quinoline, isoquinoline, furan, benzofuran, thiophene, benzothiophene, pyrazole, triazole, tetrahydropyran, tetrahydrothiopyran, piperidine and tetrahydrofuran. The group Het may be unsubstituted or substituted as defined previously. Preferred substituents (if present) include $CF_3$, $C_{1-4}$alkyl (especially methyl), $C_{1-4}$alkoxycarbonyl (such as t-butoxycarbonyl), phenyl and trifluoromethylphenyl.

When A represents 1,4-phenylene, Het typically represents a monocyclic system which does not bear a phenyl or substituted phenyl substituent.

Within this embodiment, examples of groups represented by $R^4$ include: 3-pyridyl, 6-trifluoromethyl-3-pyridyl, 2-furyl, 5-(2-trifluoromethylphenyl)-2-furyl, 2-thienyl, 3-thienyl, benzothiophen-3-yl, 3-quinolinyl, benzofuran-2-yl, 6-quinolinyl, 1-phenyl-5-methylpyrazol-4-yl, furan-3-yl, 4-(pyridin-2-yl)phenyl, 4-(pyrazol-1-yl)phenyl, 4-(1,2,4-triazol-1-yl) phenyl, 4-(thiophen-2-yl)phenyl, tetrahydropyran-4-yl, (tetrahydrothiopyran-4-yl)methyl, 1-(t-butoxycarbonyl)piperidin-4-yl, (tetrahydropyran-4-yl)methyl, 4-(pyridin-4-yl) phenyl, 4-(pyridin-3-yl)phenyl and tetrahydrofuran-2-yl.

In an alternative embodiment, $R^4$ represents H or hydrocarbon of up to 12 carbon atoms which optionally bears up to 3 substituents selected from halogen, perfluoro$C_{1-4}$alkyl, CN, $Si(R^6)_3$, OH, $C_{1-4}$alkoxy and $OCF_3$. Hydrocarbon groups represented by $R^4$ may be linear, branched or cyclic, or may comprise any combination of linear, branched and cyclic moieties having a maximum of 12 carbon atoms. Said hydrocarbon groups may be fully saturated or may contain one or more double or triple bonds, or any combination thereof, including aromatic rings. Typical examples of hydrocarbon groups represented by $R^4$ include linear or branched alkyl, alkenyl and alkynyl groups containing up to 12 carbon atoms, $C_{3-6}$alicyclic groups, $C_{3-6}$alicyclic$C_{1-4}$alkyl groups, phenyl groups, and phenyl $C_{1-4}$alkyl groups.

Said hydrocarbon groups may be unsubstituted or may bear up to 3 substituents as defined previously. However, when more than one substituent is present on a particular hydrocarbon group, said substituents are typically attached to a phenyl ring. In a particular embodiment, hydrocarbon groups represented by $R^4$ bear not more than one substituent. Preferred substituents (if present) include halogen (e.g. Cl or F), $C_{1-4}$perfluoroalkyl (eg $CF_3$ or $C_2F_5$) and $Si(R^6)_3$ where $R^6$ is as defined previously.

In the embodiment wherein $R^5$ represents $CO_2R^7$, $R^7$ is selected from the same range of optionally substituted hydrocarbon groups as described above in connection with $R^4$. In a particular embodiment, $R^7$ represents unsubstituted or mono-substituted $C_{1-6}$alkyl where the substituent is selected from halogen (e.g. Cl or F), $C_{1-4}$perfluoroalkyl (eg $CF_3$ or $C_2F_5$) and $Si(R^6)_3$ where $R^6$ is as defined previously.

In the embodiment wherein $R^5$ represents an optionally substituted hydrocarbon group, said hydrocarbon group is selected from the same range of optionally substituted hydrocarbon groups as described above in connection with $R^4$.

$R^4$ and $R^5$ are selected so that at least one of them is other than H. In a particular embodiment neither $R^4$ nor $R^5$ represents H. In another embodiment, one of $R^4$ and $R^5$ is H and $(R^2)_p$ represents a fused benzene or cyclohexane ring, in particular a fused cyclohexane ring. $R^4$ and $R^5$ are also selected so that at least one of them comprises a silyl substituent represented by $Si(R^6)_3$ where $R^6$ is as defined previously. Suitable identities for $R^6$ include $C_{1-6}$alkyl (such as methyl, ethyl, n-propyl, isopropyl, n-butyl and t-butyl) and phenyl, and specific examples of silyl substituents represented by $Si(R^6)_3$ include trimethylsilyl, triethylsilyl and t-butyldimethylsilyl.

In a particular embodiment, $R^4$ and $R^5$ each independently represents an optionally substituted hydrocarbon group as defined previously, with the proviso that at least one of $R^4$ and $R^5$ comprises a silyl substituent represented by $Si(R^6)_3$. Examples of optionally substituted hydrocarbon groups represented by $R^4$ or $R^5$ include methyl, ethyl, n-propyl, isopropyl, n-butyl, isobutyl, t-butyl, 3-methylbutyl, 2,2-dimethylpropyl, 2-ethylbutyl, 4-methylpentyl, 3,3-dimethylbutyl, 4,4-dimethylpentyl, 3-methyl-1-butenyl, 3-methyl-3-butenyl, 3-methyl-3-butene-1-ynyl, 4-methyl-1-pentynyl, 3,3-dimethyl-1-butynyl, cyclohexyl, 2,2,2-trifluoroethyl, 3,3,3-trifluoropropyl, 4,4,4-trifluorobutyl, 2-phenylethyl, 3-methoxyprop-1-ynyl, cyclohexylethynyl, 1-methyl-3,3,3-trifluoropropyl, 2,2,3,3,3-pentafluoropropyl, hydroxymethyl, isopropoxymethyl, difluoromethoxymethyl, 4-hydroxy-3-methyl-1-butynyl, 4-hydroxy-3-methylbutyl, 2-cyclopropylethyl, 2-cyclohexylethyl, 2-(cyclohexen-1-yl) ethyl, 2-(1-hydroxycyclopentyl)ethyl, 2-(1-hydroxycyclohexyl)ethyl, 4-(trifluoromethyl)phenyl, 4-(trifluoromethyl) phenylethynyl, 2-(3-fluorophenyl)ethyl, 2-(3,5-difluorophenyl)ethyl, 2-(2,4-difluorophenyl)ethyl, 2-(3-methylphenyl)ethyl, 2-(4-t-butylphenyl)ethyl, 2-[3-(trifluoromethyl)phenyl]ethyl, 2-[4-(trifluoromethyl)phenyl] ethyl, 2-(trimethylsilyl)ethyl, 2-(triethylsilyl)ethyl, 2-(t-butyldimethylsilyl)ethyl and 4-(trimethylsilyl)phenyl.

Specific examples of optionally substituted hydrocarbon groups represented by $R^4$ or $R^5$ include 3,3,3-trifluoropropyl, 4-(trifluoromethyl)phenyl, 3,3-dimethyl-1-butynyl, 3,3,- dimethylbutyl, 2-phenylethyl, cyclohexyl, 2-(trimethylsilyl) ethyl, 2-(triethylsilyl)ethyl, 2-(t-butyldimethylsilyl)ethyl and 4-(trimethylsilyl)phenyl.

A subset of the compounds of the invention consists of the compounds of formula II:

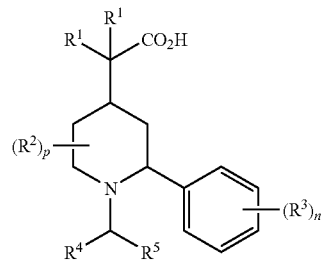

II and pharmaceutically acceptable salts and hydrates thereof; wherein n, p, $R^1$, $R^2$, $R^3$, $R^4$ and $R^5$ have the same meanings and take the same specific identities as described previously. In a particular embodiment the relative stereochemistry is as shown in formula IIA:

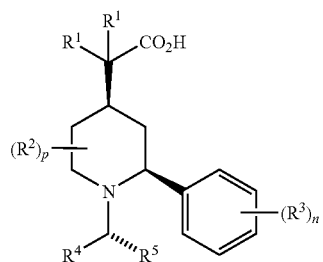

IIA

A further subset of the compounds of the invention consists of the compounds of formula III:

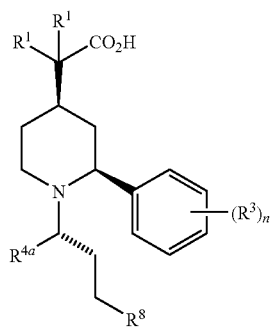

III and pharmaceutically acceptable salts and hydrates thereof; wherein:

$R^{4a}$ represents hydrocarbon of up to 12 carbon atoms which optionally bears up to 3 substituents selected from halogen, perfluoro$C_{1-4}$alkyl, CN, $Si(R^6)_3$, OH, $C_{1-4}$alkoxy and $OCF_3$;

$R^8$ represents $Si(R^6)_3$, branched $C_{1-6}$alkyl, $C_{3-6}$cycloalkyl, or phenyl which optionally bears up to 3 substituents selected from halogen, $C_{1-4}$alkyl and $CF_3$;

provided that when $R^8$ is other than $Si(R^6)_3$ then $R^{4a}$ bears at least one $Si(R^6)_3$ substituent;

and n, $R^1$, $R^3$ and $R^6$ have the same meanings and take the same specific identities as described previously.

Specific examples of compounds in accordance with the invention include those of formula IIA in which p is 0, n is 1, $R^3$ represents $CF_3$ attached in the 4-position, and $R^1$, $R^4$ and $R^5$ are as indicated in the following table:

| $R^1/R^1$ | $R^4$ | $R^5$ |
|---|---|---|
| H/H | $CH_2CH_2CF_3$ | $CH_2CH_2SiMe_3$ |
| H/H | $CH_2CH_2CF_3$ | $CH_2CH_2SiEt_3$ |
| H/H | $CH_2CH_2CF_3$ | $CH_2CH_2Si(t\text{-}Bu)Me_2$ |
| H/H | $4\text{-}CF_3\text{--}C_6H_4$ | $CH_2CH_2SiMe_3$ |
| H/H | $CH_2CH_2SiMe_3$ | $CH_2CH_2SiMe_3$ |
| H/H | $CH_2CH_2SiMe_3$ | $C\equiv C\text{-}t\text{-}Bu$ |
| H/H | $4\text{-}SiMe_3\text{-}C_6H_4$ | $CH_2CH_2SiMe_3$ |
| H/H | $4\text{-}CF_3\text{--}C_6H_4$ | $CH_2CH_2SiEt_3$ |
| H/H | $CH_2CH_2SiMe_3$ | $CH_2CH_2SiEt_3$ |
| H/H | $CH_2CH_2SiMe_3$ | $CH_2CH_2\text{-}t\text{-}Bu$ |
| H/H | $CH_2CH_2SiMe_3$ | $CH_2CH_2Ph$ |
| H/H | Cyclohexyl | $CH_2CH_2SiMe_3$ |
| H/H | $4\text{-}SiMe_3\text{-}C_6H_4$ | $CH_2CH_2SiEt_3$ |
| Me/Me | $CH_2CH_2CF_3$ | $CH_2CH_2SiMe_3$ |
| Me/Me | $4\text{-}CF_3\text{--}C_6H_4$ | $CH_2CH_2SiMe_3$ | and pharmaceutically acceptable salts or hydrates thereof.

Further examples of compounds in accordance with the invention include those of formula IIA in which p is 2, the $R^2$ groups complete a fused carbocycle, n is 1, $R^3$ represents $CF_3$ in the 4-position, each $R^1$ is H and the identities of $R^4$, $R^5$ and the fused ring are as indicated in the following table:

| Fused ring | $R^4$ | $R^5$ |
|---|---|---|
| benzene | $4\text{-}CF_3C_6H_4$ | $CH_2CH_2SiMe_3$ |
| cyclohexane | H | $CH_2CH_2SiMe_3$ | and pharmaceutically acceptable salts or hydrates thereof.

The compounds of formula I in which Z is $CO_2H$ are typically obtained by hydrolysis of the corresponding esters (1):

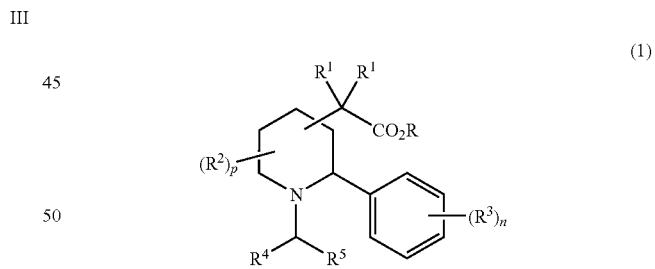

(1)

where R represents $C_{1-6}$alkyl such as methyl or ethyl, and n, $R^1$, $R^2$, $R^3$, $R^4$ and $R^5$ have the same meanings as before. The hydrolysis is typically carried out by refluxing with LiOH in aqueous THF or with NaOH or KOH in methanol.

Corresponding compounds in which Z represents 1H-tetrazol-5-yl are obtainable by conversion of the esters (1) to the corresponding nitriles, followed by treatment with azidotrimethylsilane in refluxing toluene in the presence of tributyltin oxide. The conversion to the nitrile may be carried out by adding trimethylaluminium to a suspension of ammonium chloride in toluene, then adding the ester (1), refluxing the mixture, and treating with solid potassium sodium tartrate.

Esters (1) may be obtained by reaction of compounds (2) with $R^4R^5CH\text{-}L$:

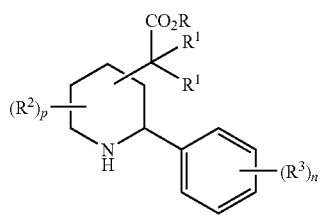

(2)

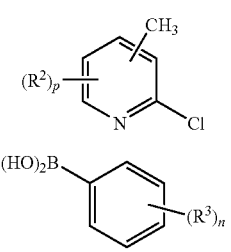

(4)

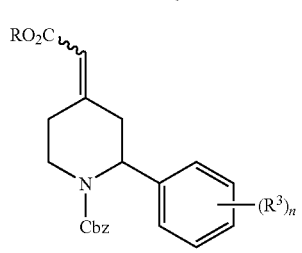

(5)

where L is a leaving group such as halide (especially bromide or iodide), tosylate, mesylate or triflate, and R, n, $R^1$, $R^2$, $R^3$, $R^4$ and $R^5$ have the same meanings as before. Normal alkylating conditions may be employed, e.g. heating in DMF solution in the presence of base such as potassium carbonate.

Alternatively, compounds (2) may undergo reductive alkylation with precursors of the group $R^4R^5CH$— which contain an aldehyde or ketone functionality. In such cases, the compound (2) may be refluxed with $R^4$—CO—$R^5$ in toluene in the presence of an acid catalyst, with azeotropic removal of water, and the resulting adduct reduced using sodium triacetoxyborohydride. In a preferred variant of this route, useful when $R^4$ is other than H and $R^5$ is an alkyn-1-yl group, a compound (2) is reacted with $R^4$—CHO and $R^5$—H in the presence of gold(III) bromide, e.g. via microwave heating at 70° C. in water.

In another variant, the compound (2), $R^4$—CHO and benzotriazole are refluxed in toluene with azeotropic removal of water, and the resulting adduct reacted with $R^5$—Zn-Hal where Hal represents halide (preferably chloride). The reaction is suitably carried out in an anhydrous aprotic solvent such as dichloromethane at reduced temperature, e.g. below 10° C.

Piperidines (2) may be obtained by hydrogenation of the corresponding pyridines (3a):

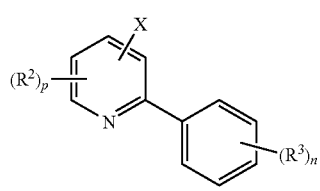

(3)

(a) X = C($R^1$)$_2$CO$_2$R
(b) X = CH$_3$ where R, n, p, $R^1$, $R^2$ and $R^3$ have the same meanings as before, e.g. in methanolic HCl over a PtO$_2$ catalyst.

Pyridines (3a) in which both $R^1$ groups are H are obtainable from the corresponding methylpyridines (3b) by treatment with CO(OR)$_2$ in the presence of strong base such as lithium diethylamide, where R has the same meaning as before. Pyridines (3a) in which one or both $R^1$ groups are other than H are obtainable by mono- or dialkylation of the pyridines (3a) in which both $R^1$ groups are H via standard methods.

Compounds (3b) may be obtained by coupling of chloropyridines (4) with arylboronic acids (5):

where n, p, $R^2$ and $R^3$ have the same meanings as before. The reaction takes place under standard Suzuki coupling conditions, e.g. in aqueous dimethoxyethane in the presence of sodium carbonate and Pd(PPh$_3$)$_4$.

An alternative route to piperidines (2) in which p is 0, both $R^1$ groups are H and the moiety CH$_2$CO$_2$R is attached to the 4-position comprises condensation of piperidones (6) with (RO)$_2$P(O)CH$_2$CO$_2$R, followed by hydrogenation of the resulting olefin (7):

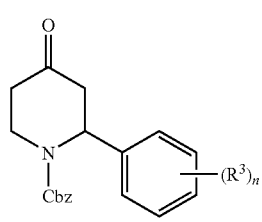

(6)

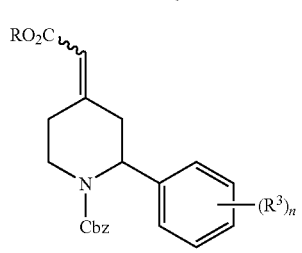

(7)

where Cbz represents benzyloxycarbonyl and R, n and $R^3$ have the same meanings as before. The condensation takes place in THF in the presence of NaH, while the hydrogenation may be carried out over a Pd/C or Pd(OH)$_2$ catalyst in ethanol and simultaneously cleaves the Cbz protecting group.

Piperidones (6) are obtainable by reduction of dihydropyridones (8):

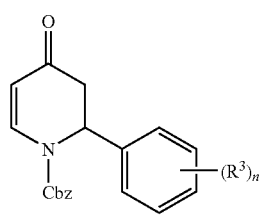

(8)

where Cbz, n and $R^3$ have the same meanings as before, e.g. using a borohydride reductant such as L-Selectride in THF at −78° C.

Dihydropyridones (8) are obtainable by reaction of 4-methoxypyridine with benzyl chloroformate and the appropriate Grignard reagent $(R^3)_nC_6H_{5-n}MgBr$ by the procedure described in Comins, *J. Heterocyclic Chem.*, (1999), 36, 1491-1500.

The above described route involving compounds (8) and (6) may be adapted to provide piperidines (2) in which p is other than zero by mono- or dialkylation of said intermediates (8) and/or (6) using $R^2$-L where $R^2$ and L have the same meanings as before. Alternatively, an $R^2$ substituent may be introduced in the 6-position by reaction of dihydropyridones (8) with $R^2$Mg-Halide in the presence of CuI in THF at −78 to −10° C., or in the presence of CuBr and $BF_3.Et_2O$ (as described by Comins, ibid.).

In a further alternative, piperidines (2) in which the moiety $C(R^1)_2CO_2R$ is attached in the 3-position may be obtained via alkylation of dihydropyridones (8) with L-$CH_2CO_2R$, followed by borohydride reduction to the corresponding piperidone as before, then removal of the ketone group by reaction with 1,2-ethanedithiol to form the dithioketal and subsequent treatment with Raney nickel.

These and other synthetic routes to piperidines (2) are described in WO 2006/043064 which is incorporated herein by reference.

A given compound in accordance with formula I, or a precursor thereof, may be converted to a different compound in accordance with formula I, or precursor thereof, by means of the standard techniques of bond formation or cleavage known to those skilled in the art of organic synthesis. For example, esters of formula (1) in which at least one $R^1$ is other than H may be prepared by alkylation of the corresponding compounds in which each $R^1$ is H by standard methods. Similarly, esters (1) in which $R^4$ and/or $R^5$ comprise unsaturation may be hydrogenated (e.g. over Raney Ni) to provide partially or fully saturated analogs.

Where they are not themselves commercially available, the starting materials for the synthetic schemes described above are available by straightforward chemical modifications of commercially available materials.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary. Alternatively, racemic intermediates in the preparation of compounds of formula I may be resolved by the aforementioned techniques, and the desired enantiomer used in subsequent steps. For example, racemic piperidine derivatives (2) may be resolved by chiral chromatography, or via salt formation with L-mandelic acid.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3$^{rd}$ ed., 1999. The protecting groups may be removed at a convenient subsequent stage using methods known from the art.

The compounds of the invention have the useful property of modifying the action of γ-secretase on amyloid precursor protein so as to selectively reduce the formation of the 1-42 isoform of Aβ, and hence find use in the development of treatments for diseases mediated by Aβ(1-42), in particular diseases involving deposition of β-amyloid in the brain.

According to a further aspect of the invention there is provided the use of a compound according to formula I as defined above, or a pharmaceutically acceptable salt or hydrate thereof, for the manufacture of a medicament for treatment or prevention of a disease associated with the deposition of β-amyloid in the brain.

The disease associated with deposition of Aβ in the brain is typically Alzheimer's disease (AD), cerebral amyloid angiopathy, HCHWA-D, multi-infarct dementia, dementia pugilistica or Down syndrome, preferably AD.

In a further aspect, the invention provides the use of a compound of Formula I as defined above, or a pharmaceutically acceptable salt or hydrate thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt or hydrate thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt or hydrate thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician,* 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.,* 56 (1999), 303-8. Further information on the differential diagnosis of MCI is provided by Knopman et al, *Mayo Clinic Proceedings,* 78 (2003), 1290-1308. In a study of elderly subjects, Tuokko et al (*Arch, Neurol.,* 60 (2003) 577-82) found that those exhibiting MCI at the outset had a three-fold increased risk of developing dementia within 5 years.

Grundman et al (*J. Mol. Neurosci.,* 19 (2002), 23-28) report that lower baseline hippocampal volume in MCI patients is a prognostic indicator for subsequent AD. Similarly, Andreasen et al (*Acta Neurol. Scand,* 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42), A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.,* 12 (1975), 196-198, Anthony et al., *Psychological Med.,* 12 (1982), 397-408; Cockrell et al., *Psychopharmacology,* 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog)(See Rosen et al., *Am. J. Psychiatry,* 141 (1984), 1356-64).

The compounds of Formula I are typically used in the form of pharmaceutical compositions comprising one or more compounds of Formula I and a pharmaceutically acceptable carrier. Accordingly, in a further aspect the invention provides a pharmaceutical composition comprising a compound of formula I as defined above, or a pharmaceutically acceptable salt thereof, and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ. Such additional compounds also include growth hormone secretagogues, as disclosed in WO 2004/110443.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature,* 423 (2003), 435-9.

Alternatively, the amyloid modifier may be a compound which inhibits the aggregation of Aβ or otherwise attenuates is neurotoxicicity. Suitable examples include chelating agents such as clioquinol (Gouras and Beal, *Neuron,* 30 (2001), 641-2) and the compounds disclosed in WO 99/16741, in particular that known as DP-109 (Kalendarev et al, *J. Pharm. Biomed. Anal.,* 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

EXAMPLES

The ability of the compounds of Formula I to selectively inhibit production of Aβ(1-42) may be determined using the following assay:

Cell-based γ-Secretase Assay

Human SH-SY5Y neuroblastoma cells overexpressing the direct γ-secretase substrate SPA4CT were induced with sodium butyrate (10 mM) for 4 hours prior to plating. Cells were plated at 35,000 cells/well/100 μl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 μl of these diluted compounds in $Me_2SO$ were further diluted into 182 μl dilution buffer (phenol red-free MEM/10% FBS, 50 mM HEPES, 1% Glutamine) and 10 μl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% $CO_2$, 25 μl and 50 μl media were transferred into a standard Meso avidin-coated 96-well plate for detection of Aβ(40) and Aβ(42) peptides, respectively. 25 μl Meso Assay buffer (PBS, 2% BSA, 0.2% Tween-20) was added to the Aβ(40) wells followed by the addition of 25 μl of the respective antibody premixes to the wells:

Aβ(40) premix: 1 μg/ml ruthenylated G2-10 antibody, 4 μg/ml biotinylated 4G8 antibody diluted in Origen buffer Aβ(42) premix: 1 μg/ml ruthenylated G2-11 antibody, 4 μg/ml biotinylated 4G8 antibody diluted in Origen buffer (Biotinylated 4G8 antibody supplied by Signet Pathology Ltd; G2-10 and G2-11 antibodies supplied by Chemicon)

After overnight incubation of the assay plates on a shaker at 4° C., the Meso Scale Sector 6000 Imager was calibrated according to the manufacturer's instructions. After washing the plates 3 times with 150 µl of PBS per well, 150 µl Meso Scale Discovery read buffer was added to each well and the plates were read on the Sector 6000 Imager according to the manufacturer's instructions.

Cell viability was measured in the corresponding cells after removal of the media for the Aβ assays by a colorimetric cell proliferation assay (CellTiter 96™ AQ assay, Promega) utilizing the bioreduction of MTS (Owen's reagent) to formazan according to the manufacturer's instructions. Briefly, 5 µl of 10×MTS/PES was added to the remaining 50 µl of media before returning to the incubator. The optical density was read at 495 nm after ~4 hours.

$LD_{50}$ and $IC_{50}$ values for inhibition of Aβ(40) and Aβ(42) were calculated by nonlinear regression fit analysis using the appropriate software (eg. Excel fit). The total signal and the background were defined by the corresponding $Me_2SO$ and inhibitor controls.

The compounds listed in the following examples all gave $IC_{50}$ values for Aβ(1-42) inhibition that were at least 2-fold lower than the corresponding $IC_{50}$ values for Aβ(1-40) inhibition, typically at least 5-fold lower, and in the preferred cases at least 50-fold lower.

Intermediate 1

(±)-Methyl {2-[4-(trifluoromethyl)phenyl]piperidin-4-yl}acetate hydrochloride

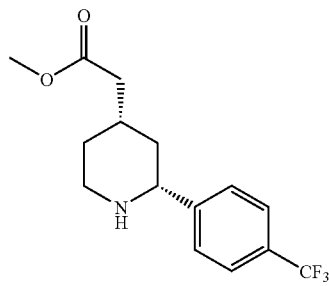 [SMILES: COC(=O)C[C@H]1CCN[C@@H](c2ccc(C(F)(F)F)cc2)C1]

Step 1:
4-Methyl-2-[4-(trifluoromethyl)phenyl]pyridine

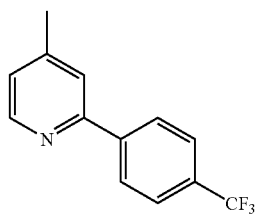 [SMILES: Cc1ccnc(-c2ccc(C(F)(F)F)cc2)c1]

A mixture of 2-chloro-4-methylpyridine (1.9 ml, 21.6 mmol) and 4-(trifluoromethyl)benzeneboronic acid (5.0 g, 26 mmol) in DME (40 ml) and aqueous $Na_2CO_3$ (2M, 40 ml) was degassed (Firestone® valve×3). Tetrakis(triphenylphosphine) palladium (0) (1.15 g, 1.0 mmol, 5 mol %) was added and following a further degassing (Firestone® valve×3) the mixture was heated at reflux for 16 hours. The reaction was cooled to room temperature diluted with $H_2O$ (100 ml) and EtOAc (150 ml). The mixture was filtered through a Celite® pad, washing through with EtOAc. The phases were separated and the aqueous layer was extracted with EtOAc (200 ml). The combined extracts were washed with $H_2O$ (100 ml) and brine (×1), then dried ($MgSO_4$), filtered and evaporated. The residue was purified by chromatography on silica, eluting with 10%) EtOAc/isohexane to give the ester (3.5 g, 68%) as a white solid. $^1$H NMR (360 MHz, $CDCl_3$) δ: 2.44 (3H, s), 7.13 (2H, d, J 5.0), 7.58 (1H, s), 7.72 (2H, d, J 8.2), 8.09 (2H, d, J 8.2), 8.57 (1H, d, J 5.0).

Step 2: Methyl {2-[4-(trifluoromethyl)phenyl]pyridin-4-yl}acetate

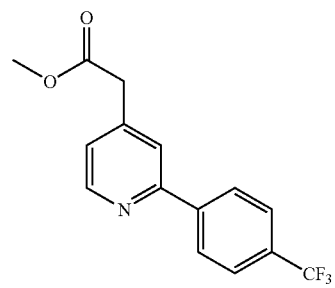 [SMILES: COC(=O)Cc1ccnc(-c2ccc(C(F)(F)F)cc2)c1]

A solution of LDA (2M in THF/heptane/ethyl benzene, 44 ml, 88 mmol) was added dropwise to a stirred solution of 4-methyl-2-[4-(trifluoromethyl)phenyl]pyridine (10.5 g, 44 mmol) in dry THF (300 ml) under $N_2$, such that the internal temperature remained <−70° C. After 1 hour at this temperature, dimethyl carbonate (8.9 ml, 106 mmol) was added. After 30 minutes the cooling bath was removed. When the internal temperature had reached −20° C. the reaction was transferred to a cold bath at −10° C., and then allowed to warm slowly to 0° C. After 1 hour at 0° C. the reaction was quenched with aqueous $NH_4Cl$ (half saturated, 100 ml). The reaction mixture was concentrated in vacuo. The residue was diluted with $H_2O$ (200 ml) and extracted with EtOAc (2×200 ml). The combined extracts were washed with brine (×1), then dried ($MgSO_4$), filtered and evaporated. The residue was purified by chromatography on silica, eluting with 10-30% EtOAc/isohexane to give the ester (9.2 g, 71%) as a pale yellow liquid. $^1$H NMR (400 MHz, $CDCl_3$) δ: 3.72 (2H, s), 3.75 (3H, s), 7.24 (1H, dd, J 1.4, 5.0), 7.72 (3H, t, J 8.4), 8.11 (2H, d, J 8.2), 8.68 (1H, d, J 5.0).

Step 3: (±)-Methyl {2-[4-(trifluoromethyl)phenyl] piperidin-4-yl}acetate hydrochloride A mixture of methyl {2-[4-(trifluoromethyl)phenyl]pyridin-4-yl}acetate (6.2 g, 21 mmol), $PtO_2$ (200 mg, 0.9 mmol) and HCl solution (4N in dioxane, 5.8 ml, 23 mmol) in MeOH (100 ml) was hydrogenated at 20 psi on a Parr® apparatus for 5 hours. The catalyst was removed by filtration and the filtrate evaporated in vacuo to give the desired piperidine as white solid (7.1 g, quant). $^1$H NMR (400 MHz, $CD_3OD$) δ: 1.58-1.72 (1H, m), 1.75-1.85 (1H, m), 2.08 (1H, d, J 14.2), 2.19 (1H, t, J 14.2), 2.28-2.38 (1H, m), 2.45 (2H, d, J 6.9), 3.24-3.32 (1H, m), 3.51-3.57 (1H, m), 3.67 (3H, s), 4.46 (1H, d, J 10.2), 7.72 (2H, d, J 8.3), 7.79 (2H, d, J 8.4).

The free base was obtained by treatment with NaHCO₃ (aq) and extraction in to DCM. The organic extracts were dried, filtered and evaporated.

Intermediate 2

(+)-Methyl {(2S,4R)-2-[4-(trifluoromethyl)phenyl]piperidin-4-yl}acetate

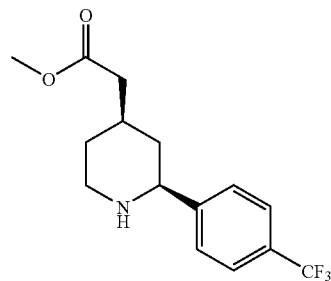 [SMILES: COC(=O)C[C@@H]1CCN[C@H](c2ccc(C(F)(F)F)cc2)C1]

(±)-cis Methyl 4-(trifluoromethyl)phenylpiperidin-4-yl)acetate (Intermediate 1 [free base], 32.6 g, 0.108 mol), was dissolved in hot isopropanol (100 ml) and the solution was added to a solution of L-(+)-mandelic acid (9 g, 0.054 mol) in hot isopropanol (170 ml) and the resulting solution was allowed to stand at room temperature overnight. A white crystalline solid was deposited (17.55 g, 36%) and was filtered. The mother liquors were evaporated and the residue was neutralized with sodium carbonate (2M, 100 ml) and extracted with dichloromethane (3×100 ml). The combined extracts were washed with brine, dried (MgSO₄), filtered and evaporated. This extract was dissolved in hot isopropanol (100 ml) and was added to a solution of D-(−)-mandelic acid (9 g, 0.054 mol) in hot isopropanol (170 ml); immediate crystallization occurred and the mixture was allowed to stand for 2 h. The white crystalline solid was isolated by filtration (21 g, 44%) and was recrystallised from isopropyl acetate (250 ml) to give the product (19.8 g, 40%) as a white crystalline material, ee>99.5%. This material was neutralized with sodium carbonate (2M, 100 ml and extracted with dichloromethane (3×100 ml). The combined extracts were washed with brine, dried (MgSO₄), filtered and evaporated to give the free base: $\alpha_D$ (c=1, MeOH)+23°; ¹H NMR (360 MHz, CDCl₃) δ: 1.23 (6H, d, J 6.9), 2.88 (1H, qn, J 6.9), 4.27 (2H, s), 7.15-7.21 (4H, m), 7.71 (2H, d, J 8.2), 8.10 (2H, d, J 8.2).

Intermediate 3

(±)-Methyl {(2R*,3S*)-2-[4-(trifluoromethyl)phenyl]piperidin-3-yl}acetate

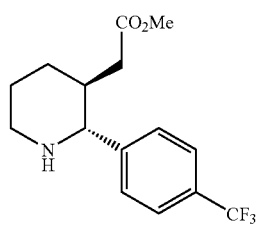 [SMILES: COC(=O)C[C@@H]1CCCN[C@H]1c1ccc(C(F)(F)F)cc1]

Step 1: (±)-Benzyl 4-oxo-2-[4-(trifluoromethyl)phenyl]-3,4-dihydropyridine-1(2H)-carboxylate

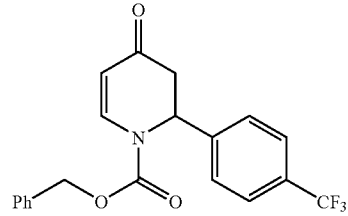 [SMILES: O=C1C=CN(C(=O)OCc2ccccc2)C(c2ccc(C(F)(F)F)cc2)C1]

4-Trifluoromethyl bromobenzene (4.2 ml, 30 mmol) was added portionwise to magnesium turnings (0.729 g, 30 mmol) in dry THF (30 ml), and two drops of 1,2-dibromoethane were added to initiate the reaction. The resulting brown solution was cooled to −25° C. 4-Methoxypyridine (3.0 ml, 30 mmol) was added followed by benzyl chloroformate (4.3 ml, 30 mmol). The reaction was stirred for 30 mins at −20° C. then quenched with 2N HCl. After stirring for 10 mins the mixture was extracted with EtOAc (×3). The combined extracts were washed with brine, dried (MgSO₄), filtered and evaporated. The residue was purified by chromatography (silica, 10-40% EtOAc/hexanes) to give the dihydropyridine (9.30 g, 83%). ¹H NMR (500 MHz, CDCl₃) δ: 2.77 (1H, d, J 16.6), 3.18 (1H, dd, J 7.7, 16.6), 5.20 (1H, d, J 12.0), 5.27 (1H, d, J 12.0), 5.42 (1H, d, J 8.3), 5.77 (1H, d, J 6.3), 7.24-7.37 (7H, m), 7.54 (2H, d, J 8.2), 8.00 (1H, m).

Step 2: (±)-Benzyl (2R*,3S*)-3-(2-methoxy-2-oxoethyl)-4-oxo-2-[4-(trifluoromethyl)phenyl]-3,4-dihydropyridine-1(2H)-carboxylate

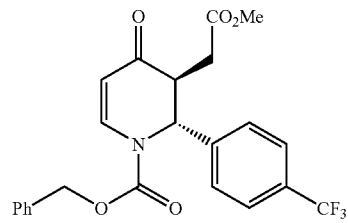 [SMILES: COC(=O)C[C@@H]1C(=O)C=CN(C(=O)OCc2ccccc2)[C@H]1c1ccc(C(F)(F)F)cc1]

A solution of the dihydropyridine from Step 1 (3.00 g, 8.0 mmol) in dry THF (80 ml) was cooled to −78° C. and lithium bis(trimethylsilyl)amide (1.0M in THF, 9.6 ml, 9.6 mmol) was added dropwise. After stirring at −78° C. for 1 hr, methyl bromoacetate (2.2 ml, 24 mmol) was added. The reaction was stirred at −78° C. for 1 hr then at 0° C. for 1.5 hrs. The reaction was quenched with saturated NH₄Cl solution. The mixture extracted with EtOAc (×3), the combined extracts were washed with brine, dried (MgSO₄), filtered and evaporated.

The residue was purified by chromatography (silica, 40% Et₂O/hexanes) to give the ester (2.74 g, 77%). ¹H NMR (360 MHz, CDCl₃) δ: 2.61-2.69 (2H, m), 3.15 (1H, dd, J 5.0, 9.8), 3.74 (3H, s), 5.18-5.28 (2H, m), 5.39 (1H, d, J 8.5), 5.70 (1H, s), 7.18-7.33 (7H, m), 7.54 (2H, d, J 8.3), 8.08 (1H, d, J 8.6).

Step 3: (±)-Benzyl (2R*,3S*)-3-(2-methoxy-2-oxo-ethyl)-4-oxo-2-[4-(trifluoromethyl)phenyl]piperidine-1-carboxylate

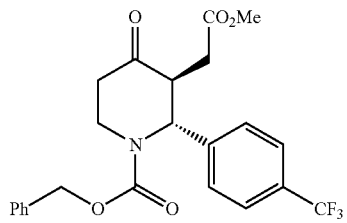 [SMILES: COC(=O)C[C@@H]1C(=O)CCN(C(=O)OCc2ccccc2)[C@H]1c1ccc(C(F)(F)F)cc1]

A solution of the enone from Step 2 (1.650 g, 3.7 mmol) in dry THF (40 ml) was cooled to −78° C. and L-selectride® (1.0M in THF, 4.6 ml, 4.6 mmol) was added. The reaction was stirred for 2 mins then quenched with saturated NH₄Cl solution. The mixture extracted with EtOAc (×3), the combined extracts were washed with brine, dried (MgSO₄), filtered and evaporated. The residue was purified by chromatography (silica, 40-50% Et₂O/hexanes) to give the ketone (1.473 g, 89%). ¹H NMR (360 MHz, CDCl₃) δ: 2.24 (1H, dd, J 4.9, 16.8), 2.57-2.70 (3H, m), 3.46-3.52 (1H, m), 3.58 (3H, s), 3.80-3.89 (1H, m), 4.57 (1H, dd, J 5.2, 14.2), 4.93-4.98 (2H, m), 5.10 (1H, d, J 12.1), 7.07 (2H, s), 7.26-7.41 (5H, m), 7.57 (2H, d, J 8.1).

Step 4: (±)-Methyl {(6S*,7R*)-7-[4-(trifluoromethyl)phenyl]-1,4-dithia-8-azaspiro[4.5]dec-6-yl}acetate

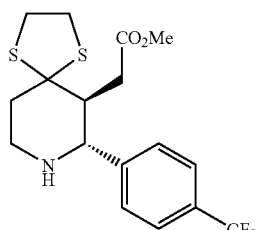

A solution of the ketone from Step 3 (0.772 g, 1.7 mmol) in DCM (20 ml) was cooled to 0° C. and 1,2-ethanedithiol (0.43 ml, 5.1 mmol) and BF₃.OEt₂ (1.27 ml, 10 mmol) were added. The reaction was stirred at RT for 48 hrs then diluted with EtOAc. The mixture was washed with 1N NaOH solution then brine, dried (MgSO₄), filtered and evaporated. The residue was purified by chromatography (silica, 30% EtOAc/hexanes) to give the dithiane (0.420 g, 63%). ¹H NMR (360 MHz, CDCl₃) δ: 2.03-2.11 (1H, m), 2.20-2.26 (1H, m), 2.35-2.43 (1H, m), 2.73-2.83 (2H, m), 3.06-3.16 (2H, m), 3.24 (3H, s), 3.25-3.32 (4H, m), 3.50 (1H, d, J 9.9), 7.47-7.58 (4H, m).

Step 5: (±)-Methyl {(2R*,3S*)-2-[4-(trifluoromethyl)phenyl]piperidin-3-yl}acetate Raney nickel (slurry in water) was added portionwise to a solution of the dithiane from Step 4 (0.418 g, 1.1 mmol) in MeOH (20 ml). The reaction was heated under reflux for 3 hrs then allowed to cool. The reaction was filtered through Hyflo® and the solvent was evaporated. The resulting mixture was extracted with DCM, dried (MgSO₄), filtered and evaporated. The residue was purified by chromatography (silica, 2% MeOH/DCM) to give the piperidine (0.168 g, 52%). ¹H NMR (360 MHz, CDCl₃) δ: 1.21-1.26 (1H, m), 1.69-1.75 (2H, m), 1.90-2.10 (4H, m), 2.72-2.80 (1H, m), 3.16 (1H, m), 3.36 (1H, d, J 9.7), 3.50 (3H, s), 7.48 (2H, d, J 8.1), 7.57 (2H, d, J 8.2).

Intermediate 4

Methyl 2-methyl-2-{(2S,4R)-2-[4-(trifluoromethyl)phenyl]piperidin-4-yl}propanoate

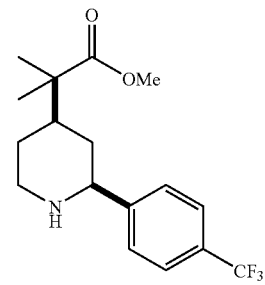 [SMILES: COC(=O)C(C)(C)[C@@H]1CCN[C@H](c2ccc(C(F)(F)F)cc2)C1]

Step 1: Methyl 2-methyl-2-{2-[4-(trifluoromethyl)phenyl]pyridin-4-yl}propanoate

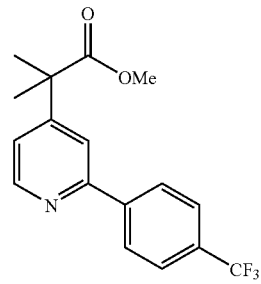 [SMILES: COC(=O)C(C)(C)c1ccnc(-c2ccc(C(F)(F)F)cc2)c1]

Methyl {2-[4-(trifluoromethyl)phenyl]pyridin-4-yl}acetate (Intermediate 1, step 2) (1.0 g, 3.39 mmol) in THF (8 ml) was cooled to −78° C. and treated with NaHMDS (2 M, 3.7 ml, 7.4 mmol) dropwise, such that the internal temperature remained <−70° C. After 45 min, MeI (0.46 ml, 7.37 mmol) was added dropwise. After the reaction mixture was stirred at −70° C. for 1 hour, the cooling bath was removed and the mixture was allowed to warm slowly to 0° C. LC/MS showed it was a mixture of mono- and di-methyl product. The reaction mixture was cooled to −78° C. again, NaHMDS (2M, 2.0 ml, 4.0 mmol) was added dropwise and after 40 min at −70° C., MeI (0.25 ml, 4.0 mmol) was added dropwise. After 50 min, the reaction mixture was warmed to 0° C., the reaction quenched with aqueous NH$_4$Cl, extracted with CH$_2$Cl$_2$, the organic phase washed with brine, dried over MgSO$_4$, filtered and concentrated. The crude product was purified by chromatography (silica, 12-100% EtOAc/hexanes) to give the dimethylpyridine ester (0.59 g, 54%). $^1$H NMR (600 MHz, CDCl$_3$) δ 1.57 (6H, s), 3.62 (3H, s), 7.20 (1H, dd, J 2.0, 5.3), 7.63 (1H, s), 7.65 (2H, dd, J 1.1, 10.6), 8.03 (2H, d, J 8.0), 8.58 (1H, dd, J 0.9, 5.3).

Step 2: Methyl 2-methyl-2-{2-[4-(trifluoromethyl)phenyl]piperidin-4-yl}propanoate

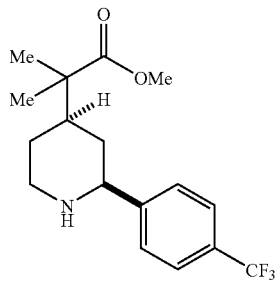 [SMILES: COC(=O)C(C)(C)[C@@H]1CCN[C@H](c2ccc(C(F)(F)F)cc2)C1]

A mixture of dimethylpyridine ester from step 1 (0.44 g, 1.35 mmol), PtO$_2$ (45 mg), HCl solution (4N in dioxane, 0.36 ml) and MeOH (6 ml) was hydrogenated at 24 psi on a Parr apparatus for 6 hours. The catalyst was removed by filtration and the filtrate was evaporated to give a white solid, which was treated with NaHCO$_3$ (sat.) and extracted into DCM. The combined organic layer was washed with brine, dried over MgSO$_4$, filtered and concentrated to afford the dimethylpiperidine ester (0.41 g, 92%) confirmed by MS (ESI+): cal'd [M+H]$^+$ 330.2, exp. 330.0.

Step 3: Methyl 2-methyl-2-{(2S,4R)-2-[4-(trifluoromethyl)phenyl]piperidin-4-yl}propanoate The racemic dimethylpiperidine ester (0.41 g) from step 2 was resolved on Chiralcel OJ column (Solvent: 15% IPA/Heptane) to give methyl 2-methyl-2-{(2S,4R)-2-[4-(trifluoromethyl)phenyl]piperidin-4-yl}propanoate (100.7 mg) and methyl 2-methyl-2-{(2R,4S)-2-[4-(trifluoromethyl)phenyl]piperidin-4-yl}propanoate (77.0 mg).

Example 1

((2S,4R)-2-[4-(trifluoromethyl)phenyl]-1-{(1S)-4,4,4-trifluoro-1-[2-(trimethylsilyl)ethyl]butyl}-4-piperidinyl)acetic acid

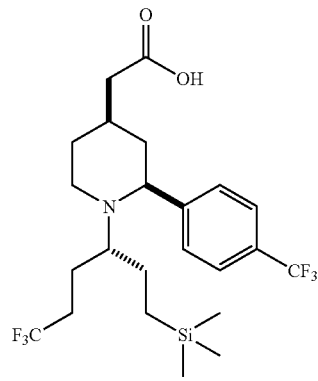 [SMILES: C[Si](C)(C)CC[C@H](CCC(F)(F)F)N1CC[C@@H](CC(=O)O)C[C@H]1c1ccc(C(F)(F)F)cc1]

Step 1
A solution of Intermediate 2 (1.00 g, 3.32 mmol), 4,4,4-trifluorobutyraldehyde (628 mg, 4.98 mmol), trimethylsilyl acetylene (920 □L, 6.64 mmol), and AuBr$_3$ (72 mg, 0.166 mmol) in H$_2$O (3.0 mL) was heated at 75° C. for 4 h. The reaction mixture was concentrated, dissolved in CH$_2$Cl$_2$ (2 mL), and purified by flash chromatography (0-100% Et$_2$O/hexanes) to give 713 mg (42%) of the desired acetylene as a colorless oil confirmed by MS (ESI+): cal'd [M+H]$^+$ 508.2, exp. 508.2.

Step 2
To a solution of the acetylene from Step 1 (713 mg, 1.40 mmol) in EtOH (10 mL) was added PtO$_2$ (200 mg, 0.881 mmol). After 18 h under 60 psi H$_2$, the reaction mixture was filtered over Celite and concentrated. The crude oil was purified by flash chromatography (0-50% Et$_2$O/hexanes) to give 88 mg (12%) of the saturated silane piperidine methyl ester as a colorless oil confirmed by MS (ESI+): cal'd [M+H]$^+$ 512.2, exp. 512.2.

Step 3
To a solution of the piperidine methyl ester from Step 2 (88 mg, 0.172 mmol) in THF (0.8 mL), MeOH (0.2 mL) and water (0.2 mL) was added LiOH (4.9 mg, 0.21 mmol). After 16 h at room temperature, the reaction mixture was treated with 1N HCl (0.3 mL). The solution was concentrated and purified by reverse phase HPLC (25-100% CH$_3$CN/H$_2$O with 0.05% TFA) to give 77 mg (73%) of ((2S,4R)-2-[4-(trifluoromethyl)phenyl]-1-{(1S)-4,4,4-trifluoro-1-[2-(trimethylsilyl)ethyl]butyl}-4-piperidinyl)acetic acid TFA salt as a white powder confirmed by MS (ESI+): cal'd [M+H]$^+$ 498.2, exp. 498.2. $^1$H NMR (600 MHz, CD$_3$OD) δ −0.15 (m, 2H), −0.05 (s, 9H), 1.17 (m, 1H), 1.65 (m, 1H), 1.95 (m, 1H), 2.17 (sextet, 4H, J=15.0), 2.33 (m, 3H), 3.42 (t, 1H, J=11.8), 3.60 (d, 1H, J=11.7), 4.00, (dd, 1H, J=10.9, 3.1), 4.92 (d, 2H, J=11.5), 7.52 (d, 2H, J=8.1), 7.78 (d, 2H, J=8.1), 7.86 (s, 2H), 7.92 (d, 2H, J=7.8).

Examples 2-13

Examples 2-13 were made by the procedures in Example 1 using Intermediate 2 and the appropriate aldehyde and acetylene in Step 1.

| Example | Structure | Name | M/Z ES+ [MH]+ |
|---|---|---|---|
| 2 | 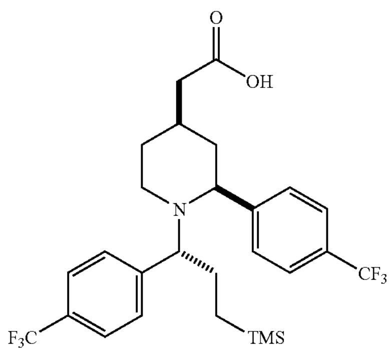 [SMILES: C[Si](C)(C)CC[C@H](c1ccc(C(F)(F)F)cc1)N1CC[C@@H](CC(=O)O)C[C@H]1c1ccc(C(F)(F)F)cc1] | {(2S,4R)-2-[4-(trifluoromethyl)phenyl]-1-[(1R)-1-[4-(trifluoromethyl)phenyl]-3-(trimethylsilyl)propyl]piperidin-4-yl}acetic acid | 546.0 |
| 3 | 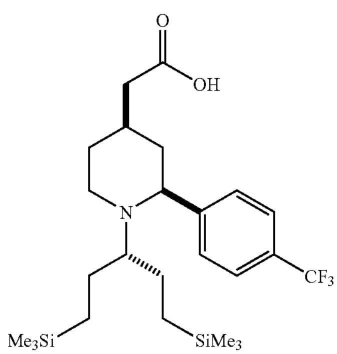 | ((2S,4R)-2-[4-(trifluoromethyl)phenyl]-1-{3-(trimethylsilyl)-1-[2-(trimethylsilyl)ethyl]propyl}piperidin-4-yl)acetic acid | 502.2 |
| 4 | 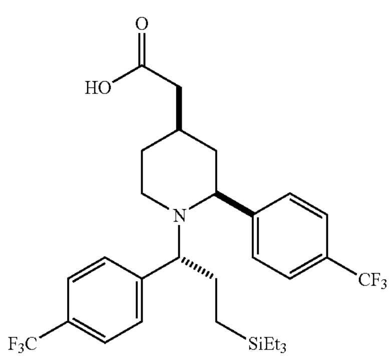 | {(2S,4R)-1-{(1R)-3-(triethylsilyl)-1-[4-(trifluoromethyl)phenyl]propyl}-2-[4-(trifluoromethyl)phenyl]piperidin-4-yl}acetic acid | 588.4 |
| 5 | 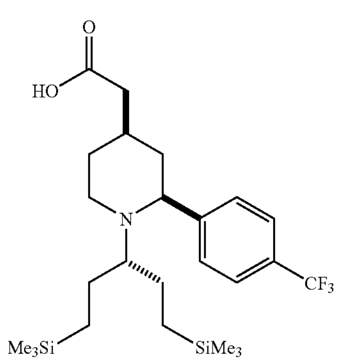 | {(2S,4R)-1-{(1S)-3-(triethylsilyl)-1-[2-(trimethylsilyl)ethyl]propyl}-2-[4-(trifluoromethyl)phenyl]piperidin-4-yl}acetic acid | 544.1 |

-continued

| Example | Structure | Name | M/Z ES+ [MH]+ |
|---|---|---|---|
| 6 | 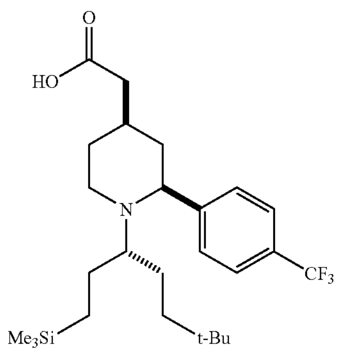 [SMILES: CC(C)(C)CC[C@H](CC[Si](C)(C)C)N1CC[C@@H](CC(=O)O)C[C@H]1c1ccc(C(F)(F)F)cc1] | {(2S,4R)-1-{(1R)-4,4-dimethyl-1-[2-(trimethylsilyl)ethyl]pentyl}-2-[4-(trifluoromethyl)phenyl]piperidin-4-yl}acetic acid | 486.2 |
| 7 | 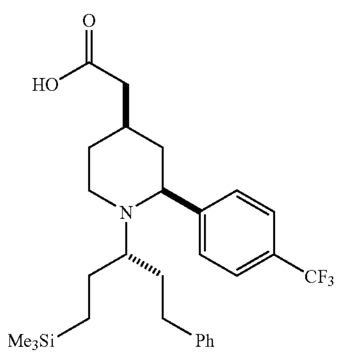 [SMILES: C[Si](C)(C)CC[C@@H](CCc1ccccc1)N1CC[C@@H](CC(=O)O)C[C@H]1c1ccc(C(F)(F)F)cc1] | {(2S,4R)-1-{(1R)-3-phenyl-1-[2-(trimethylsilyl)ethyl]propyl}-2-[4-(trifluoromethyl)phenyl]piperidin-4-yl}acetic acid | 506.3 |
| 8 | 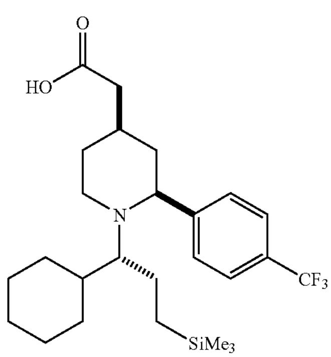 [SMILES: C[Si](C)(C)CC[C@H](C1CCCCC1)N1CC[C@@H](CC(=O)O)C[C@H]1c1ccc(C(F)(F)F)cc1] | {(2S,4R)-1-[(1R)-1-cyclohexyl-3-(trimethylsilyl)propyl]-2-[4-(trifluoromethyl)phenyl]piperidin-4-yl}acetic acid | 484.1 |
| 9 | 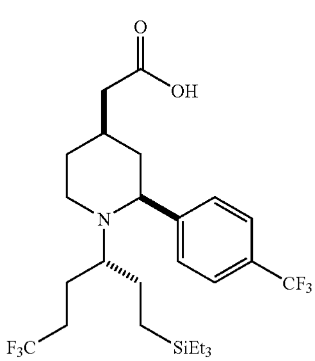 | ((2S,4R)-2-[4-(trifluoromethyl)phenyl]-1-{(1S)-4,4,4-trifluoro-1-[2-(triethylsilyl)ethyl]butyl}piperidin-4-yl)acetic acid | 540.2 |

-continued

| Example | Name | M/Z ES+ [MH]+ |
|---|---|---|
| 10 | {(2S,4R)-1-((1S)-1-{2-[tert-butyl(dimethyl)silyl]ethyl}-4,4,4-trifluorobutyl)-2-[4-(trifluoromethyl)phenyl]piperidin-4-yl}acetic acid | 540.2 |
| 11 | ((2S,4R)-2-[4-(trifluoromethyl)phenyl]-1-{(1R)-3-(trimethylsilyl)-1-[4-(trimethylsilyl)phenyl]propyl}piperidin-4-yl)acetic acid | 550.3 |
| 12 | {(2S,4R)-1-{(1R)-3-(triethylsilyl)-1-[4-(trimethylsilyl)phenyl]propyl}-2-[4-(trifluoromethyl)phenyl]piperidin-4-yl}acetic acid | 592.2 |
| 13 | {(2S,4R)-1-{(1R)-4,4-dimethyl-1-[4-(trimethylsilyl)phenyl]pentyl}-2-[4-(trifluoromethyl)phenyl]piperidin-4-yl}acetic acid | 534.3 |

Example 14

2-methyl-2-((2S,4R)-2-[4-(trifluoromethyl)phenyl]-1-{(1S)-4,4,4-trifluoro-1-[2-(trimethylsilyl)ethyl]butyl}piperidin-4-yl)propanoic acid

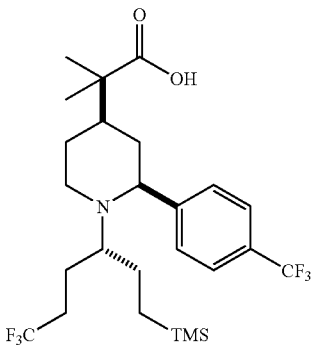 [SMILES: CC(C)(C(=O)O)[C@@H]1CCN([C@@H](CCC(F)(F)F)CC[Si](C)(C)C)[C@H](c2ccc(C(F)(F)F)cc2)C1]

C., 20 min consecutively. Then, the reaction mixture was acidified with 1N HCl to pH ~4 and purified by reverse phase HPLC (25-100% CH₃CN/H₂O with 0.05% TFA) to give 16.3 mg (18%) of 2-methyl-2-((2S,4R)-2-[4-(trifluoromethyl)phenyl]-1-{(1S)-4,4,4-trifluoro-1-[2-(trimethylsilyl)ethyl]butyl}piperidin-4-yl)propanoic acid TFA salt as a white solid confirmed by MS (ESI+): cal'd [M+H]⁺ 526.2, exp. 526.0. ¹H NMR (600 MHz, CD₃OD) δ 0.04 (9H, s), 0.01-0.10 (1H, m), 0.44 (1H, dt, J=4.4, 14.0), 1.17 (3H, s), 1.18 (3H, s), 1.40-1.51 (1H, m), 1.85-2.38 (10H, m), 2.75 (1H, br s), 3.15-3.28 (1H, m), 3.71 (1H, d, J=9.4), 4.73 (1H, br s), 7.71 (2H, br s), 7.83 (2H, d, J=7.6).

Example 15

Example 15 was made by the procedures in Example 14 using Intermediate 4 and 4-(trifluoromethyl)benzaldehyde in Step 1.

| Example | Structure | Name | M/Z ES⁺ [MH]⁺ |
|---|---|---|---|
| 15 | 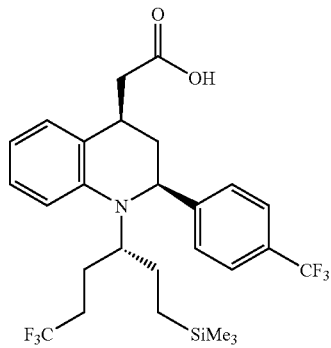 | 2-methyl-2-{(2S,4R)-2-[4-(trifluoromethyl)phenyl]-1-[(1R)-1-[4-(trifluoromethyl)phenyl]-3-(trimethylsilyl)propyl]piperidin-4-yl}propanoic acid | 574.2 |

Step 1
A solution of Intermediate 4 (67 mg, 0.203 mmol), 4,4,4-trifluorobutyraldehyde (90.1 mg, 0.715 mmol), trimethylsilyl acetylene (77 mg, 0.784 mmol), and AuBr₃ (15.1 mg, 0.035 mmol) in H₂O (0.4 mL) was heated at 75° C. for 2 h. The reaction mixture was diluted with CH₂Cl₂. The organic layer was washed with NaHCO₃(sat.), dried and concentrated to afford crude product, which was purified by reversed phase HPLC to afford TFA salt (80.6 mg). After base extraction, the reaction afforded the desired acetylene (54.8 mg, 50%) confirmed by MS (ESI+): cal'd [M+H]⁺ 536.2, exp. 536.0.

Step 2
To a solution of the acetylene from Step 1 (54.8 mg, 0.102 mmol) in EtOH (1 mL) was added 10% Pd/C (36.2 mg). The resulting mixture was hydrogenated at r.t. After 20 hours, the mixture was diluted with MeOH and filtered though Celite. The filtrate was concentrated to afford crude saturated silane dimethyl piperidine ester (77.5 mg) confirmed by MS (ESI+): cal'd [M+H]⁺540.3, exp. 540.1. This crude product was hydrolyzed directly.

Step 3
To a solution of the crude dimethyl piperidine ester from Step 2 (77.5 mg, 0.144 mmol) in THF (0.3 mL), MeOH (0.2 mL) and water (0.2 mL) was added LiOH (8.0 mg, 0.334 mmol). The vial was heated under microwave at 120° C., 10 min, 160°

Example 16

2-[4-(trifluoromethyl)phenyl]-1-{4,4,4-trifluoro-1-[2-trimethylsilyl)ethyl]butyl}-1,2,3,4-tetrahydro-quinolin-4-yl)acetic acid

Step 1: 4-methyl-2-[4-(trifluoromethyl)phenyl]quinoline

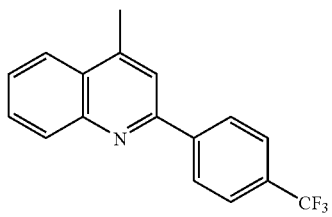 [SMILES: Cc1cc(-c2ccc(C(F)(F)F)cc2)nc2ccccc12]

To a degassed mixture of 2-chlorolepidine (4.67 g, 26.3 mmol), 4-(trifluoromethyl)phenylboronic acid (5.0 g, 26.3 mmol) and Na$_2$CO$_3$ (13.94 g, 132 mmol) in EtOH (110 mL) was added tetrakis(triphenylphosphine) palladium (1.52 g, 1.315 mmol). The reaction mixture was refluxed for 4 hr and then cooled to room temperature, diluted with EtOAc (200 mL), and filtered through a Celite pad, washing with EtOAc (25 mL). The solution was concentrated and purified by chromatography, eluting with 0-50% EtOAc/hexanes to give 7.56 g (quantitative yield) of the desired aryl quinoline as an orange oil confirmed by MS (ESI+): cal'd [M+H]$^+$ 288.3, exp. 288.0.

Step 2: methyl {2-[4-(trifluoromethyl)phenyl]quinolin-4-yl}acetate

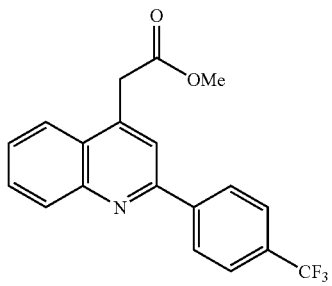 [SMILES: COC(=O)Cc1cc(-c2ccc(C(F)(F)F)cc2)nc2ccccc12]

To a cooled (−78° C.) solution of LDA (110 mmol prepared by the addition of 44 mL of 2.5 M butyllithium to 15.5 mL of diisopropylamine) in THF (45 mL) was added the aryl quinoline from Sep 1 (10.52 g, 36.6 mmol) dropwise in THF (50 mL) followed by TMEDA (6.6 ml), such that the internal temperature remained below −70° C. After 1 h of stirring at −78° C., dimethyl carbonate (9.25 mL, 110 mmol) was added dropwise. When the internal temperature had reached −10° C., the reaction was warmed to 0° C. with an ice bath. After 1 hour at 0° C., the reaction was quenched with sat'd. aqueous NH$_4$Cl (25 mL) and concentrated in vacuo. The residue was diluted with H$_2$O (25 mL) and extracted with EtOAc (2×50 mL). The combined extracts were washed with brine (25 mL), then dried over Na$_2$SO$_4$, filtered and concentrated. The residue was purified by chromatography, eluting with 10-30% EtOAc/hexane to give 8.90 g (70%) of the desired methyl ester as a yellow waxy solid confirmed by MS (ESI+): cal'd [M+H]$^+$ 346.3, exp. 346.0.

Step 3: methyl {2-[4-(trifluoromethyl)phenyl]-1,2,3,4-tetrahydroquinolin-4-yl}acetate

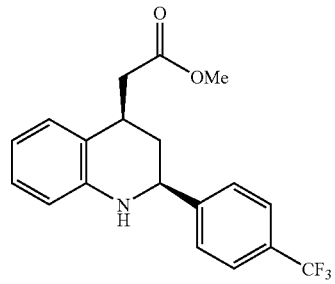 [SMILES: COC(=O)C[C@H]1C[C@@H](c2ccc(C(F)(F)F)cc2)Nc2ccccc21]

A mixture of the methyl ester from Step 2 (3.15 g, 9.12 mmol) and PtO$_2$ (621 mg, 2.74 mmol) in MeOH (47 mL) and acetic acid (3 mL) was reduced under 50 psi H$_2$ on the Parr® shaker for 1 hour. The catalyst was removed by filtration and the filtrate evaporated in vacuo. The free base was obtained by treatment with NaHCO$_3$ (aq) and extraction in to DCM. The combined extracts were washed with brine, then dried (Na$_2$SO$_4$), filtered and evaporated. The residue was purified by chromatography, eluting with 2% EtOAc/hexanes to give 1.62 g (51%) of the desired tetrahydroquinoline as a yellow waxy solid confirmed by MS (ESI+): cal'd [M+H]$^+$ 350.4, exp. 350.0.

Step 4: methyl (2-[4-(trifluoromethyl)phenyl]-1-{4,4,4-trifluoro-1-(trimethylsilyl)ethynyl]butyl}-1,2,3,4-tetrahydroquinolin-4-yl)acetate

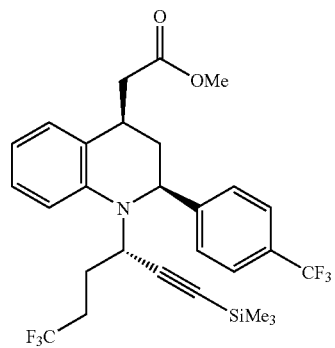 [SMILES: COC(=O)C[C@H]1C[C@@H](c2ccc(C(F)(F)F)cc2)N([C@H](C#C[Si](C)(C)C)CCC(F)(F)F)c2ccccc21]

A solution of the tetrahydroquinoline from Step 3 (253 mg, 0.72 mmol), 4,4,4-trifluorobutyraldehyde (365 mg, 2.70 mmol), trimethylsilyl acetylene (401 µL, 6.64 mmol), and AuBr$_3$ (95 mg, 0.22 mmol) in H$_2$O (1 mL) was heated at 75° C. overnight. The reaction mixture was reloaded two more times with aldehyde, acetylene and catalyst and heated at 75° C. for an additional 30 hr. The reaction mixture was diluted with EtOAc and filtered through a Celite pad, washing with EtOAc. The solution was concentrated and purified by chromatography, eluting with 11-13% EtOAc/hexanes to give 250 mg (62%) of the desired trimethylsilyl acetylene as a colorless oil confirmed by MS (ESI+): cal'd [M+H]⁺ 556.6, exp. 556.0.

Step 5: methyl (2-[4-(trifluoromethyl)phenyl]-1-{4,4,4-trifluoro-1-[2-(trimethylsilyl)ethyl]butyl}-1,2,3,4-tetrahydroquinolin-4-yl)acetate

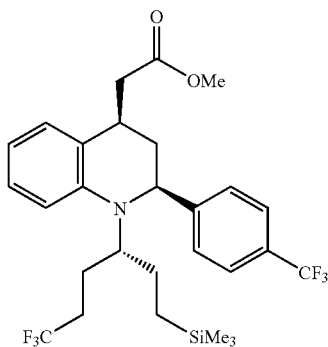 [SMILES: COC(=O)C[C@H]1C[C@@H](c2ccc(C(F)(F)F)cc2)N([C@@H](CCC(F)(F)F)CC[Si](C)(C)C)c2ccccc21]

To a solution of the trimethylsilyl acetylene from Step 4 (250 mg, 0.45 mmol) in EtOH (3.25 mL) was added 10 wt % Pd/C (96 mg, 0.090 mmol) and stirred for 22 hr at room temperature under 1 atm $H_2$. The reaction mixture was diluted with DCM (5 mL) and filtered over Celite while rinsing with additional DCM (5 mL) followed by MeOH (5 mL). The solution was concentrated and the residue purified by chromatography, eluting with 5% MeOH/hexanes to give 240 mg (81%) of the silane methyl ester as a colorless oil confirmed by MS (ESI+): cal'd [M+H]⁺ 560.7, exp. 560.0

Step 6: 2-[4-(trifluoromethyl)phenyl]-1-{(1S)-4,4,4-trifluoro-1-[2-trimethylsilyl)ethyl]butyl}-1,2,3,4-tetrahydroquinolin-4-yl)acetic acid

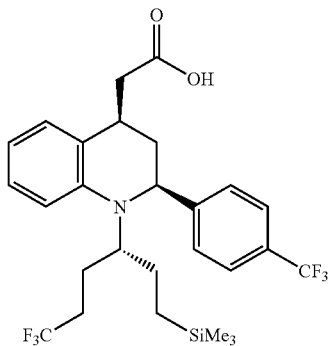 [SMILES: C[Si](C)(C)CC[C@H](CCC(F)(F)F)N1c2ccccc2[C@@H](CC(=O)O)C[C@H]1c1ccc(C(F)(F)F)cc1]

To a solution of the silane methyl ester from Step 5 (240 mg, 0.43 mmol) in THF (1.2 mL) was added aqueous LiOH (51 mg, 2.14 mmol in 1.2 mL $H_2O$) and the reaction mixture stirred overnight at 55° C. The reaction mixture was diluted with DCM (2 mL), acidified with 1M HCl (3 mL) and extracted with DCM (3×5 mL). The combined organic phases were washed with brine, concentrated and purified by chromatography, eluting with 20-55% EtOAc/hexanes to give 87 mg (37%) of the desired acid as a tan solid confirmed by MS (ESI+): cal'd [M+H]⁺ 546.6, exp. 546.0. ¹H NMR (600 MHz, CDCl₃) δ: −0.12 (9H, quartet, J=4.9), 0.14 (1H, s), 0.33 (1H, sextet, J=7.3), 1.45-1.63 (4H, m), 1.63-1.75 (1H, m), 1.86-1.99 (2H, m), 2.19 (1H, dd, J=16.2, 9.3), 2.35 (1H, qd, J=7.6, 4.3), 2.85 (1H, dd, J=16.2, 5.1), 3.24 (1H, dt, J=9.2, 4.6), 3.35 (1H, s), 4.51 (1H, dd, J=8.9, 5.8), 6.77 (1H, m), 6.84 (1H, d, J=7.9), 7.02 (1H, d, J=7.6), 7.15 (1H, quartet, J=5.1), 7.38 (2H, d, J=8.1), 7.52 (2H, d, J=8.1).

Example 17

{2-[4-(trifluoromethyl)phenyl]-1-[3-(trimethylsilyl)propyl]decahydroquinolin-4-yl}acetic acid

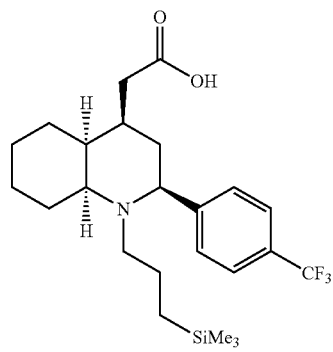 [SMILES: C[Si](C)(C)CCCN1[C@H](c2ccc(C(F)(F)F)cc2)C[C@H](CC(=O)O)[C@@H]2CCCC[C@@H]21]

Step 1: methyl {2-[4-(trifluoromethyl)phenyl]decahydroquinolin-4-yl}acetate

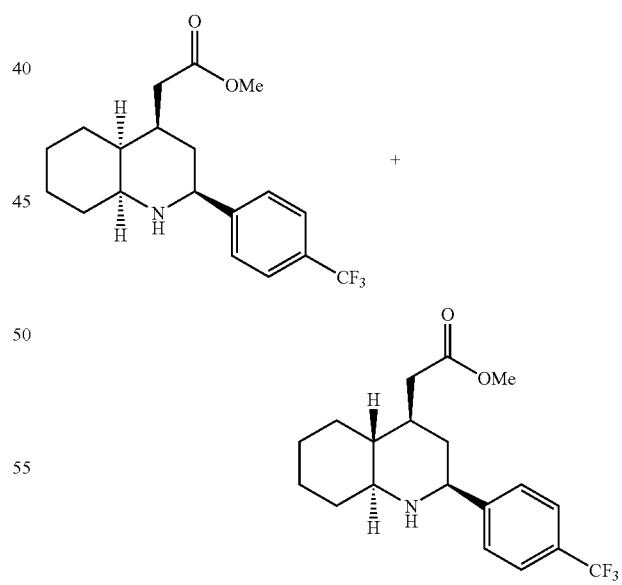

A mixture of aryl quinoline from Example 16 Step 2 (8.11 g, 23.5 mmol) and PtO₂ (1.067 g, 4.70 mmol) in MeOH (104 mL) and acetic acid (13 mL) was reduced under 50 psi $H_2$ on the Parr® shaker overnight. The reaction mixture was then filtered and concentrated in vacuo. The free base was obtained by treatment with sat.'d aq. NaHCO₃ (50 mL) and extraction with DCM (3×75 mL). The combined organics were washed with brine (1×25 mL), then dried over Na$_2$SO$_4$, filtered and concentrated. The residue was purified by chromatography, eluting with 0-10% MeOH/1:1 hexanes/DCM to give 6.88 g (82%) of a cis/trans mixture of decahydroquinoline diastereomers as a yellow oil confirmed by MS (ESI+): cal'd [M+H]$^+$ 356.4, exp. 356.1.

Step 2: methyl {2-[4-(trifluoromethyl)phenyl]-1-[3-(trimethylsilyl)prop-2-yn-1-yl]decahydroquinolin-4-yl}acetate

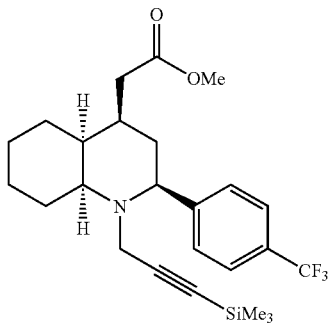 [SMILES: COC(=O)C[C@H]1C[C@@H](c2ccc(C(F)(F)F)cc2)N(CC#C[Si](C)(C)C)[C@H]2CCCC[C@@H]12]

A solution of the cis/trans mixture of decahydroquinoline diastereomers (1.20 g, 3.48 mmol), formaldehyde (1.1 mL, 13.9 mmol) as a 37 wt % solution in H$_2$O, trimethylsilyl acetylene (963 μL, 6.95 mmol), and AuBr$_3$ (455 mg, 1.04 mmol) in H$_2$O (2.0 mL) was heated at 75° C. overnight. LC/MS of an aliquot showed the reaction had not gone to completion. The reaction mixture was charged with a second portion of formaldehyde (1.1 mL, 13.9 mmol) as a 37 wt % solution in H$_2$O and trimethylsilyl acetylene (963 μL, 6.95 mmol) and heated at 75° C. for an additional 72 hr. The reaction mixture was diluted with EtOAc and filtered through a Celite pad, washing with EtOAc (25 mL). The solution was concentrated and purified by chromatography, eluting with 0-20% EtOAc/hexanes to give 413 mg (26%) of the cis-decahydroquinoline trimethylsilyl acetylene as a colorless oil confirmed by MS (ESI+): cal'd [M+H]$^+$ 466.6, exp. 466.1.

Step 3: methyl {2-[4-(trifluoromethyl)phenyl]-1-[3-(trimethylsilyl)propyl]decahydroquinolin-4-yl}acetate

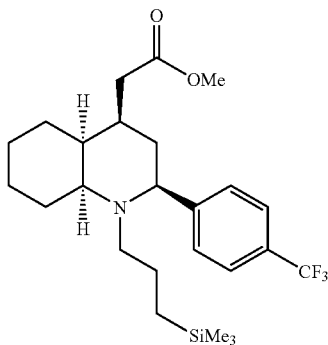

To a solution of the cis-decahydroquinoline trimethylsilyl acetylene from Step 2 (413.3 mg, 0.736 mmol) in EtOH (3.2 mL) was 10 wt % Pd/C (96 mg, 0.090 mmol) and stirred at room temperature for 24 hr under 1 atm H$_2$. The reaction mixture was diluted with DCM (5 mL) and filtered over Celite while rinsing with DCM (5 mL) followed by MeOH (5 mL). The solution was concentrated and the residue purified by chromatography, eluting with 0-15% EtOAc/hexanes to give 220 mg (53%) of the silane methyl ester as a colorless oil confirmed by MS (ESI+): cal'd [M+H]$^+$ 470.7, exp. 470.1.

Step 4: {2-[4-(trifluoromethyl)phenyl]-1-[3-(trimethylsilyl)propyl]decahydroquinolin-4-yl}acetic acid

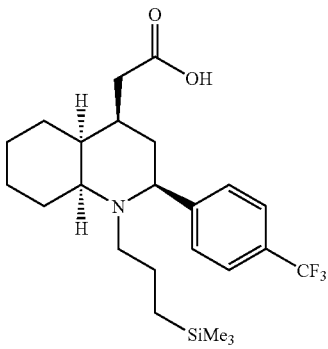 [SMILES: C[Si](C)(C)CCCN1[C@H](c2ccc(C(F)(F)F)cc2)C[C@H](CC(=O)O)[C@@H]2CCCC[C@@H]21]

To a solution of the silane methyl ester from Step 3 (220 mg, 0.468 mmol) in THF (750 μL) was added aqueous KOH (131 mg, 2.342 mmol in 500 μL water) and the reaction mixture stirred overnight at 55° C. MeOH (250 μL) was then added and the reaction mixture heated at 60° C. for an additional 48 hr. The reaction mixture was diluted with DCM (2 mL), acidified with 1M HCl (5 mL) and extracted with DCM (3×5 mL). The combined organics were washed with brine (1×5 mL), concentrated and purified by chromatography, eluting with 0-10% MeOH/DCM to give 87 mg (41%) of the desired acid as a colorless oil confirmed by MS (ESI+): cal'd [M+H]$^+$ 456.6, exp. 456.1. $^1$H NMR (600 MHz, CDCl$_3$) δ: –0.10-0.21 (9H, m), –0.036 (1H, ddd, J=15.4, 10.1, 4.5), 0.01-0.02 (1H, m), 1.18-1.35 (4H, m), 1.35-1.56 (4H, m), 1.56-1.72 (2H, m), 1.87 (2H, dd, J=23.1, 12.6), 2.03 (1H, d, J=13.9), 2.06-2.24 (2H, m), 2.107 (1H, s), 2.29 (1H, dd, J=15.1, 6.0), 2.46 (1H, t, J=11.1), 2.71 (1H, s), 3.57 (1H, d, J=4.8), 7.34-7.79 (4H, m).

Examples 18-23

Examples 18-23 were made by analogous procedures to Example 1 using the appropriate arylboronic acid in step 1 of Intermediate 1.

| Example | Structure | Name | M/Z ES+ [MH]+ |
|---------|-----------|------|---------------|
| 18 | 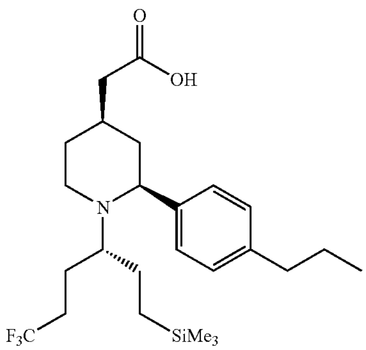 [SMILES: CCCc1ccc([C@@H]2C[C@H](CC(=O)O)CCN2[C@@H](CCC(F)(F)F)CC[Si](C)(C)C)cc1] | (±)-(2-(4-propylphenyl)-1-{4,4,4-trifluoro-1-[2-(trimethylsilyl)ethyl]butyl}piperidin-4-yl)acetic acid | 472.1 |
| 19 | 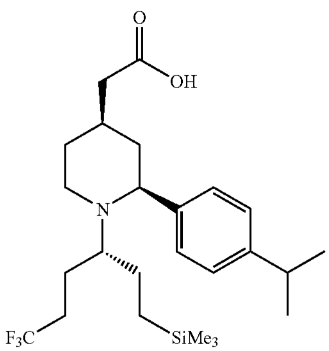 [SMILES: CC(C)c1ccc([C@@H]2C[C@H](CC(=O)O)CCN2[C@@H](CCC(F)(F)F)CC[Si](C)(C)C)cc1] | (+)-(2-(4-isopropylphenyl)-1-{4,4,4-trifluoro-1-[2-(trimethylsilyl)ethyl]butyl}piperidin-4-yl)acetic acid | 472.1 |
| 20 | 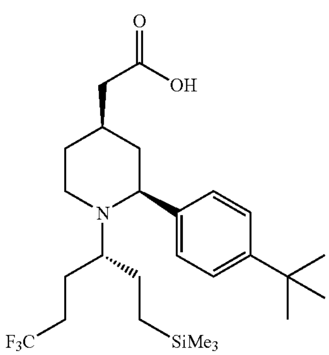 [SMILES: CC(C)(C)c1ccc([C@@H]2C[C@H](CC(=O)O)CCN2[C@@H](CCC(F)(F)F)CC[Si](C)(C)C)cc1] | (+)-(2-(4-tert-butylphenyl)-1-{4,4,4-trifluoro-1-[2-(trimethylsilyl)ethyl]butyl}piperidin-4-yl)acetic acid | 486.2 |
| 21 | 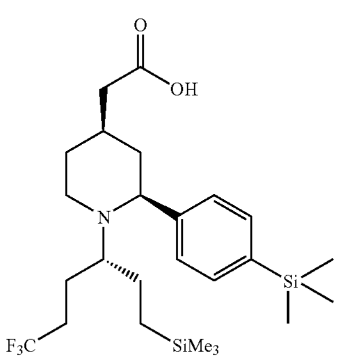 [SMILES: C[Si](C)(C)CC[C@H](CCC(F)(F)F)N1CC[C@@H](CC(=O)O)C[C@H]1c1ccc([Si](C)(C)C)cc1] | (±)-1-{4,4,4-trifluoro-1-[2-(trimethylsilyl)ethyl]butyl}-2-[4-(trimethylsilyl)phenyl]piperidin-4-yl}acetic acid | 502.1 |

| Example | Structure | Name | M/Z ES+ [MH]+ |
|---|---|---|---|
| 22 | 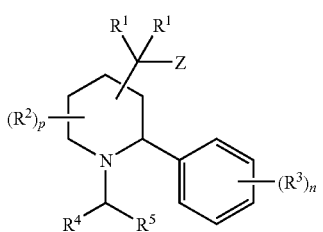 | (±)-(2-[4-(trifluoromethoxy)phenyl]-1-{4,4,4-trifluoro-1-[2-(trimethylsilyl)ethyl]butyl}pipendin-4-yl)acetic acid | 514.1 |
| 23 | 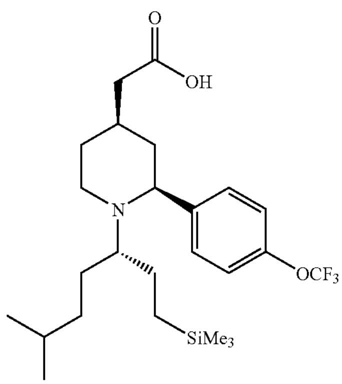 [SMILES: CC(C)CC[C@@H](CC[Si](C)(C)C)N1CC[C@@H](CC(=O)O)C[C@H]1c1ccc(OC(F)(F)F)cc1] | (+)-{1-{4-methyl-1-[2-(trimethylsilyl)ethyl]pentyl}-2-[4-(trifluoromethoxy) phenyl]piperidin-4-yl}acetic acid | 488.2 |

The invention claimed is:

1. A compound of formula I:

I or a pharmaceutically acceptable salt thereof; wherein:
p is 0, 1 or 2;
n is 0, 1, 2 or 3;
the moiety —C(R$^1$)$_2$—Z is attached to the 3-, 4- or 5-position of the piperidine ring;
Z represents CO$_2$H or a tetrazole ring;
each R$^1$ independently represents H or a non-aromatic hydrocarbon group of up to 6 carbon atoms; or the two R$^1$ groups complete a C$_{3-6}$alicyclic group;
each R$^2$ independently represents a non-aromatic hydrocarbon group of up to 6 carbon atoms;
each R$^3$ independently represents halogen, C$_{1-6}$alkyl bearing 0-3 fluorine substituents, C$_{1-6}$alkoxy bearing 0-3 fluorine substituents, C$_{2-6}$alkenyl, or Si(R$^6$)$_3$;
R$^4$ is selected from:
(i) H;
(ii) Het-A- where A represents a bond, CH$_2$ or 1,4-phenylene and Het represents a heterocyclic ring system of up to 10 ring atoms which optionally bears up to 3 substituents selected from halogen, C$_{1-4}$alkyl, CF$_3$, Si(R$^6$)$_3$, C$_{1-4}$-alkoxy and C$_{1-4}$-alkoxycarbonyl or which optionally bears a phenyl substituent which itself is optionally substituted with halogen, C$_{1-4}$alkyl, Si(R$^6$)$_3$, C$_{1-4}$-alkoxy or C$_{1-4}$alkoxycarbonyl; and
(iii) hydrocarbon of up to 12 carbon atoms which optionally bears up to 3 substituents selected from halogen, perfluoroC$_{1-4}$alkyl, CN, Si(R$^6$)$_3$, OH, C$_{1-4}$-alkoxy and OCF$_3$;

R$^5$ is selected from:
(i) H;
(ii) hydrocarbon of up to 12 carbon atoms which optionally bears up to 3 substituents selected from halogen, perfluoroC$_{1-4}$-alkyl, CN, Si(R$^6$)$_3$, OH, C$_{1-4}$-alkoxy and OCF$_3$; and
(iii) CO$_2$R$^7$ where R$^7$ represents hydrocarbon of up to 12 carbon atoms which optionally bears up to 3 substituents selected from halogen, perfluoroC$_{1-4}$-alkyl, CN, Si(R$^6$)$_3$, OH, C$_{1-4}$-alkoxy and OCF$_3$; and each R$^6$ independently represents a hydrocarbon group of up to 6 carbon atoms;

provided R$^4$ and R$^5$ do not both represent H and provided at least one of R$^4$ and R$^5$ bears Si(R$^6$)$_3$ as a substituent.

2. A compound according to claim 1 or a pharmaceutically acceptable salt thereof, wherein the moiety —C(R$^1$)$_2$—Z is attached to the 4-position of the piperidine ring.

3. A compound according to claim 1, or a pharmaceutically acceptable salt thereof, wherein $R^4$ and $R^5$ each independently represents a hydrocarbon group of up to 12 carbon atoms which optionally bears up to 3 substituents selected from halogen, perfluoro$C_{1-4}$alkyl, CN, Si$(R^6)_3$, OH, $C_{1-4}$alkoxy and OCF$_3$; provided at least one of $R^4$ and $R^5$ bears a silyl substituent represented by Si$(R^6)_3$.

4. A compound according to claim 1 defined by formula II:

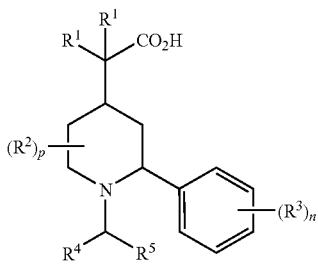

II or a pharmaceutically acceptable salt thereof.

5. A compound according to claim 4 or a pharmaceutically acceptable salt thereof, wherein the relative stereochemistry is as shown in formula IIA:

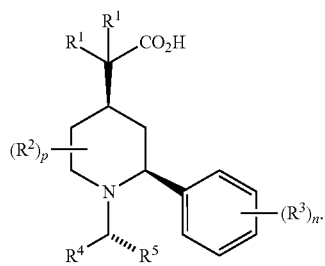

IIA

6. A compound according to claim 5 defined by formula III:

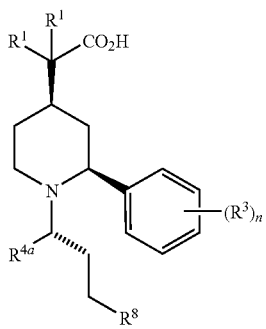

III or a pharmaceutically acceptable salt thereof wherein:

$R^{4a}$ represents hydrocarbon of up to 12 carbon atoms which optionally bears up to 3 substituents selected from halogen, perfluoro$C_{1-4}$alkyl, CN, Si$(R^6)_3$, OH, $C_{1-4}$alkoxy and OCF$_3$; and $R^8$ represents Si$(R^6)_3$, branched $C_{1-6}$alkyl, $C_{3-6}$cycloalkyl, or phenyl which optionally bears up to 3 substituents selected from halogen, $C_{1-4}$alkyl and CF$_3$;

provided that when $R^8$ is other than Si$(R^6)_3$ then $R^{4a}$ bears at least one Si$(R^6)_3$ substituent.

7. A compound according to claim 5, wherein p is 0, n is 1, $R^3$ represents CF$_3$ attached in the 4-position, and $R^1$, $R^4$ and $R^5$ are as indicated in the following table:

| $R^1/R^1$ | $R^4$ | $R^5$ |
|---|---|---|
| H/H | CH$_2$CH$_2$CF$_3$ | CH$_2$CH$_2$SiMe$_3$ |
| H/H | CH$_2$CH$_2$CF$_3$ | CH$_2$CH$_2$SiEt$_3$ |
| H/H | CH$_2$CH$_2$CF$_3$ | CH$_2$CH$_2$Si(t-Bu)Me$_2$ |
| H/H | 4-CF$_3$—C$_6$H$_4$ | CH$_2$CH$_2$SiMe$_3$ |
| H/H | CH$_2$CH$_2$SiMe$_3$ | CH$_2$CH$_2$SiMe$_3$ |
| H/H | CH$_2$CH$_2$SiMe$_3$ | C≡C-t-Bu |
| H/H | 4-SiMe$_3$-C$_6$H$_4$ | CH$_2$CH$_2$SiMe$_3$ |
| H/H | 4-CF$_3$—C$_6$H$_4$ | CH$_2$CH$_2$SiEt$_3$ |
| H/H | CH$_2$CH$_2$SiMe$_3$ | CH$_2$CH$_2$SiEt$_3$ |
| H/H | CH$_2$CH$_2$SiMe$_3$ | CH$_2$CH$_2$-t-Bu |
| H/H | CH$_2$CH$_2$SiMe$_3$ | CH$_2$CH$_2$Ph |
| H/H | Cyclohexyl | CH$_2$CH$_2$SiMe$_3$ |
| H/H | 4-SiMe$_3$-C$_6$H$_4$ | CH$_2$CH$_2$SiEt$_3$ |
| Me/Me | CH$_2$CH$_2$CF$_3$ | CH$_2$CH$_2$SiMe$_3$ |
| Me/Me | 4-CF$_3$—C$_6$H$_4$ | CH$_2$CH$_2$SiMe$_3$ | or a pharmaceutically acceptable salt thereof.

8. A compound according to claim 5 wherein p is 0, n is 1, $R^3$ is attached in the 4-position, each $R^1$ is H and $R^3$, $R^4$ and $R^5$ are as indicated in the following table:

| $R^3$ | $R^4$ | $R^5$ |
|---|---|---|
| n-propyl | CH$_2$CH$_2$CF$_3$ | CH$_2$CH$_2$SiMe$_3$ |
| Isopropyl | CH$_2$CH$_2$CF$_3$ | CH$_2$CH$_2$SiMe$_3$ |
| t-butyl | CH$_2$CH$_2$CF$_3$ | CH$_2$CH$_2$SiMe$_3$ |
| SiMe$_3$ | CH$_2$CH$_2$CF$_3$ | CH$_2$CH$_2$SiMe$_3$ |
| OCF$_3$ | CH$_2$CH$_2$CF$_3$ | CH$_2$CH$_2$SiMe$_3$ |
| OCF$_3$ | CH$_2$CH$_2$CH(Me)$_2$ | CH$_2$CH$_2$SiMe$_3$ | or a pharmaceutically acceptable salt thereof.

9. A pharmaceutical composition comprising a compound according to claim 1 or a pharmaceutically acceptable salt thereof, and a pharmaceutically acceptable carrier.

* * * * *